(12) United States Patent
Turcott

(10) Patent No.: US 7,558,627 B1
(45) Date of Patent: Jul. 7, 2009

(54) SYSTEM AND METHOD FOR RAPID OPTIMIZATION OF CONTROL PARAMETERS OF AN IMPLANTABLE CARDIAC STIMULATION DEVICE

(75) Inventor: Robert G. Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 854 days.

(21) Appl. No.: 10/674,710

(22) Filed: Sep. 29, 2003

(51) Int. Cl.
*A61N 1/00* (2006.01)
(52) U.S. Cl. .................................................. 607/27
(58) Field of Classification Search ............ 607/25, 607/27, 28, 30, 17, 9; 600/510
See application file for complete search history.

(56) References Cited

U.S. PATENT DOCUMENTS

| | | | |
|---|---|---|---|
| 5,476,483 A | 12/1995 | Bornzin et al. | 607/17 |
| 5,487,752 A * | 1/1996 | Salo et al. | 607/17 |
| 5,549,650 A * | 8/1996 | Bornzin et al. | 607/24 |
| 5,643,327 A * | 7/1997 | Dawson et al. | 607/24 |
| 5,800,471 A * | 9/1998 | Baumann | 607/25 |
| 6,371,922 B1 | 4/2002 | Baumann et al. | 600/485 |
| 6,409,675 B1 | 6/2002 | Turcott | 600/508 |
| 6,477,406 B1 | 11/2002 | Turcott | 600/518 |
| 6,491,639 B1 | 12/2002 | Turcott | 600/508 |
| 6,522,923 B1 | 2/2003 | Turcott | 607/27 |
| 6,527,729 B1 | 3/2003 | Turcott | 600/528 |
| 6,561,984 B1 | 5/2003 | Turcott | 600/485 |
| 6,575,912 B1 | 6/2003 | Turcott | 600/485 |
| 2001/0031993 A1 | 10/2001 | Salo et al. | 607/9 |

OTHER PUBLICATIONS

Pappone et al. (2000). "Cardiac Pacing In Heart Failure Patients With Left Bundle Branch Block: Impact Of Pacing Site For Optimizing Left Ventricular Resynchronization." Ital Heart J 1(7): 464-9.
Auricchio et al. (1999). "The Pacing Therapies For Congestive Heart Failure (Path-Chf) Study: Rationale, Design, And Endpoints Of A Prospective Randomized Multicenter Study." Am J Cardiol 83(5B): 130D-135D.

* cited by examiner

*Primary Examiner*—George Manuel
(74) *Attorney, Agent, or Firm*—Theresa Takeuchi; Steven M. Mitchell

(57) ABSTRACT

Techniques are provided for rapidly optimizing control parameters of pacemakers or implantable cardioverter defibrillators. Briefly, the heart is paced using different sets of control parameters during a sequence of consecutive short evaluation periods of equal duration, which each last only about 5-12 seconds. Transient cardiac performance is monitored during each of the short evaluation phases and optimal parameter settings are then estimated based on changes in the transient cardiac performance from one parameter setting to another. By using a series of consecutive short evaluation periods of equal duration, rather than switching between short test periods and longer baseline periods, the overall duration of the test can be reduced as compared to predecessor techniques that require long intervening baseline periods.

21 Claims, 18 Drawing Sheets

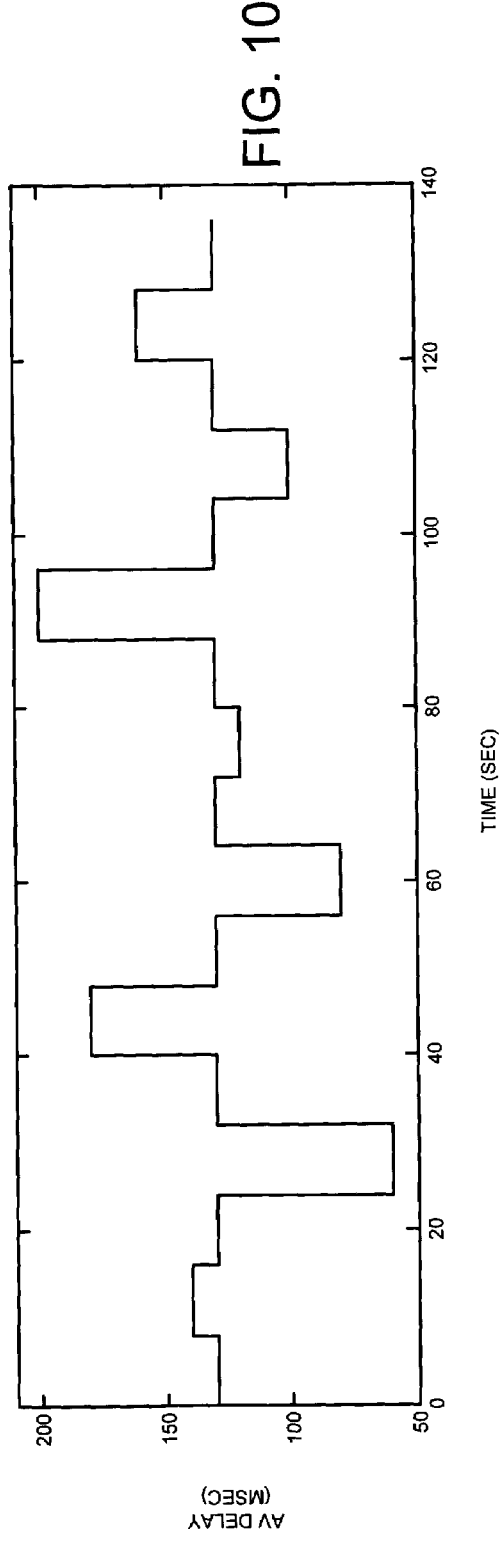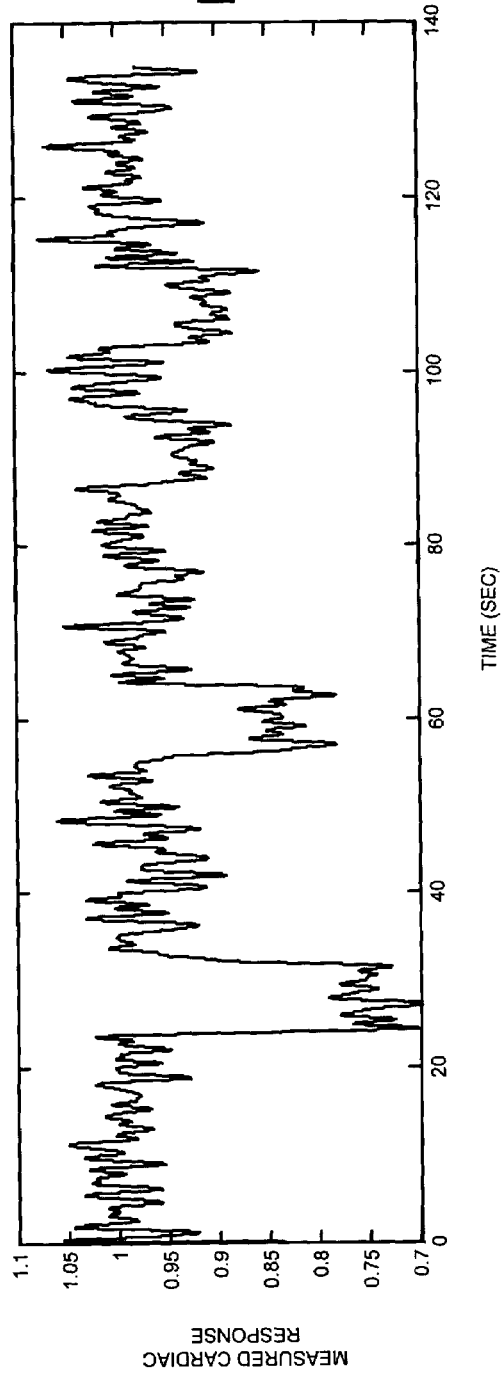

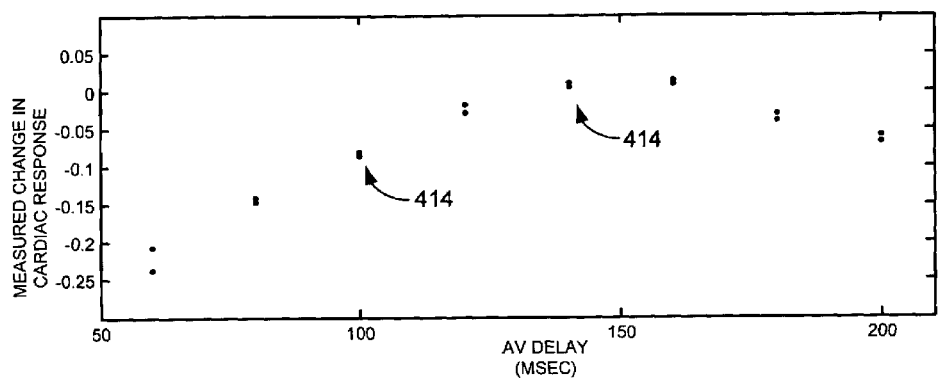

SYSTEM AND METHOD FOR RAPID OPTIMIZATION OF CONTROL PARAMETERS OF AN IMPLANTABLE CARDIAC STIMULATION DEVICE

FIELD OF THE INVENTION

The invention generally relates to implantable cardiac stimulation devices and to external programmer devices used in connection therewith and in particular to techniques for optimizing pacing control parameters to achieve improved hemodynamic performance.

BACKGROUND OF THE INVENTION

Implantable cardiac stimulation devices, particularly pacemakers and implantable cardioverter defibrillators (ICDs), are usually configured to be used in conjunction with an external programmer which enables a physician to program the operation of an implanted device to, for example, control the specific parameters by which the pacemaker detects arrhythmia conditions and responds thereto. For instance, the physician may specify the sensitivity with which the pacemaker or ICD senses electrical signals within the heart and also specify the amount of electrical energy to be employed in pacing pulses or defibrillation shocks. Another common control parameter is the atrioventricular (AV) delay, which for dual chamber devices specifies the time delay between a paced or sensed atrial event and a ventricular output pulse. Additionally, the external programmer may be configured to receive and display a wide variety of diagnostic information detected by the implantable device, such as intracardiac electrogram (IEGM) signals sensed by the device.

Insofar as programming is concerned, some control parameters specify operational algorithms to be performed by the implanted device including, for example, the mode of the device, such as whether the device is to operate in a dual-chambered mode or a single-chambered mode, the type of response to be performed if a pacemaker mediated tachycardia (PMT) or a pre-ventricular contraction (PVC) is detected, and whether any rate responsive sensors of the device are to be turned on or off (such as minute ventilation sensors). Other control parameters specify particular values to be use such as the pacing base rate, maximum tracking rate, minimum tracking rate, sensor rate, sensor slope, sensor threshold or AV delay of the implanted device. Together, the various control parameters permit the operation of the cardiac stimulation device to be tailored to the needs of a particular patient to provide optimal therapy while minimizing the risk of any unnecessary therapy. State of the art implantable cardiac stimulation devices may have dozens or hundreds of programmable parameters that can be individually programmed using the external programmer.

For many patients, particularly those with congestive heart failure (CHF), it is desirable to identify a set of control parameters that will yield optimal cardiac performance (also referred to as hemodynamic performance). Cardiac performance is a measure of the overall effectiveness of the cardiac system of a patient and is typically represented in terms of, one or more of, stroke volume, cardiac output, end-diastolic volume, end-systolic volume, ejection fraction, cardiac output index, pulmonary capillary wedge pressure, central venous pressure. Stroke volume is the amount of blood ejected from the left ventricle during systole. Cardiac output is the volume of blood pumped by the left ventricle per minute (or stroke volume times the heart rate). End-diastolic volume is the volume of blood in the chamber at the end of the diastolic phase, when the chamber is at its fullest. End-systolic volume is the volume of blood in the chamber at the end of the systolic phase, when the chamber contains the least volume. Ejection fraction is percentage of the end-diastolic volume ejected by the ventricle per beat. Cardiac index is the volume of blood ejected per minute normalized to the body surface area of the patient. Other factors representative of cardiac performance include the contractility of the left ventricle, the maximum rate of change of pressure with time (i.e. max dP/dt) or the maximum flow through mitral valve. Pulmonary capillary wedge pressure reflects filling pressure of the left ventricle. Central venous pressure reflects the fluid status of the patient. Cardiac performance can be assessed in a variety of ways, such as by measuring stroke volume using Doppler echocardiography, nuclear imaging, or thermodilution; or by measuring dP/dt using a pressure catheter. Pulmonary capillary wedge pressure can be measured using a pressure catheter in the pulmonary artery. Central venous pressure can be measured using a pressure catheter in the right ventricle or left atrium.

In view of the importance of maintaining optimal cardiac performance, especially for patients with compromised cardiac function, it would be desirable to provide improved techniques for use with pacemakers or ICDs for identifying pacing control parameters that optimize cardiac performance, particularly to reduce the degree of heart failure. It is to this end that aspects of the invention are generally directed.

For example, it is desirable to identify the AV delay value providing the best cardiac performance. In normal patients, the electrical conduction through the AV node is intact, and the body automatically adjusts the delay via the circulating hormones and the autonomic nervous system according to its physiologic state. It is well known, for example, that in normal patients the AV delay shortens with increasing heart rate. For patients with abnormal AV node conduction or complete heart block, a pacemaker can control the AV delay by delivering a ventricular pacing pulse at a software-controlled delay after an atrial pace or atrial sensed event. Since the optimum AV delay varies from person to person, this parameter must be optimized on an individual basis. Conventionally, the physician attempts to program the AV delay (or other parameters) for a given patient by using an external programmer to control the device implanted within the patient to cycle through a set of different AV delay values. For each value, the implanted device paces the heart of the patient for at least a few minutes to permit hemodynamic equilibration, then the physician records a measure of the resulting cardiac performance. The AV delay value that yields the best cardiac performance is then selected and programmed into the device.

Test phases for a conventional optimization procedure wherein each phase lasts four minutes are illustrated within FIG. 1. FIG. 2 illustrates a simulated cardiac performance curve 2 as a function of AV delay. Each triangle 4 in FIG. 2 represents the cardiac performance achieved at a particular test value of the AV delay. Circle 6 identifies the optimal AV delay value (normalized to 1). The traditional view has been that two to five minutes at each parameter setting is necessary to allow the cardiovascular system of the patient to equilibrate to provide reliable values of the resulting cardiac performance. Unfortunately, this can be time consuming—particularly if there are several different parameters to be optimized. In the example of FIG. 2, with eight different AV delay values tested using four minutes per value, thirty-two minutes is required just to obtain data to optimize the AV delay. Thus, the approach is not amenable to anything other than infrequent use in implantable devices.

One proposed technique for reducing the time required to optimize pacing parameters is set forth in U.S. Pat. No. 5,487, 752 to Salo, et al. Briefly, Salo, et al. suggest that parameter optimization can be achieved by alternating between baseline pacing parameters and test pacing parameters, with the baseline parameters used for periods of about twenty heart beats and test parameters used for periods of about five beats. The test phases of this technique are illustrated within FIG. 3. According to Salo, et al., by limiting test periods to only five beats at a time and by alternating between test periods and considerably longer baseline periods, the cardiovascular system remains substantially in a baseline hemodynamic state and hemodynamic feedback systems are not significantly influenced, permitting the effects of the test parameters to be reliably determined despite the short test periods. As a result, Salo et al. assert that pacing parameters can be more quickly optimized than with predecessor techniques that pace for several minutes at each of the various test settings. Salo, et al. state that a ratio of 4:1 of baseline pacing to test pacing is desired to ensure that that the cardiovascular system remains substantially in the baseline hemodynamic state so that relatively short test periods can be accommodated. Assuming a heart rate of 60 beats per minute (bpm), the technique of Salo et al. would appear to still require about nearly 3½ minutes to complete an AV delay test using eight different AV delay values.

A related technique is set forth in U.S. Pat. No. 5,800,471 to Baumann et al. wherein a 3:1 ratio of baseline pacing to test parameter pacing is employed. Again the extended baseline period appears to be provided to allow for the hemodynamic system to return to a state of equilibrium between brief test periods.

Although the techniques of Salo, et al. and Baumann et al. appear to provide improvement over conventional techniques, it would be desirable to achieve an even greater reduction in parameter optimization times and it is to this end that further aspects of the invention are drawn. In particular, it is desirable to provide a technique for parameter optimization that would be sufficiently fast to allow for very frequent or semi-continuous parameter optimization so as to allow control parameters to be updated more or less continuously based upon the current needs of the patient. For example, the parameters could be updated to reflect changes in patient posture to provide a different set of control parameters optimized for use while the patient is standing as opposed to sitting or optimized for use while the patient is exercising as opposed to resting. As can be appreciated, with sufficiently fast parameter optimization, control parameters could be updated to provide optimal pacing for the patient at all times. It is to this end that still other aspects of the invention are drawn.

AV delay is just one example of a pacing parameter that is preferably optimized to achieve the best possible cardiac performance. Another is interventricular delay, which specifies the time delay between pacing pulses delivered to the right and left ventricles. In this regard, one factor associated with heart failure is asynchronous activation of the ventricles such that the mechanical contraction is not coordinated effectively thus compromising cardiac performance. As a result, the pumping ability of the heart is diminished and the patient experiences shortness of breath, fatigue, swelling, and other debilitating symptoms. The weakened heart is also susceptible to potentially lethal ventricular tachyarrhythmias. A decrease in cardiac performance can result from a progression of heart failure. In many cases, the interventricular delay can be adjusted to help improve cardiac performance and reduce the degree of heart failure, effectively reducing symptoms and improving the quality of life.

One particularly promising technique for reducing the risk of heart failure is "cardiac resynchronization therapy", which seeks to normalize asynchronous cardiac electrical activation and the resultant asynchronous contractions by delivering synchronized pacing stimulus to both ventricles using pacemakers or ICDs equipped with biventricular pacing capability. The stimulus is synchronized so as to help to improve overall cardiac performance. This may have the additional beneficial effect of reducing the susceptibility to life-threatening tachyarrhythmias. In any case, biventricular pacing control parameters, such as interventricular delay, need to be adjusted so as to synchronize the ventricles and to optimize patient cardiac performance. As with the optimization of AV delay values, the optimization of interventricular delay values or other cardiac resynchronization therapy controls values can be time consuming.

Accordingly, it is also desirable to provide rapid optimization techniques for a wide variety of control parameters, particularly including parameters related to cardiac resynchronization therapy and the invention is directed to this end as well.

SUMMARY OF THE INVENTION

Techniques are provided for rapidly optimizing control parameters of an implantable cardiac stimulation device. Briefly, the implantable device is controlled to deliver therapy to the heart of the patient while switching among different sets of control parameters during a series of consecutive evaluation periods that are substantially equal in duration to one another. Values representative of transient cardiac performance corresponding to the different sets of parameters are detected. The optimal set of control parameters for use in maximizing cardiac performance is then estimated based on the values representative of transient cardiac performance. In one example, the consecutive evaluation periods are each only eight seconds in duration.

By using a series of consecutive short evaluation periods of equal duration, rather than switching between short test periods and longer baseline periods, the overall duration of the test can be reduced as compared to predecessor techniques employing the longer intervening baseline periods. An important aspect of the invention is the recognition that optimal control parameters can be reliably estimated based on transient cardiac performance without requiring that the cardiovascular system of the patient otherwise remain near a baseline equilibrium state for the duration of the optimization procedure. In other words, there is no need to wait for hemodynamic feedback systems to return the cardiovascular system to an equilibrium state following each short test period, and before new test parameters are applied. Rather, optimal parameters can be determined based entirely on transient cardiac performance as detected during consecutive, short evaluation periods. Hence, long baseline periods are not required and so optimization can proceed more rapidly.

In one example, the implantable device is controlled to switch directly from one set of test parameters to another through the series of consecutive evaluation periods. In another example, each short test parameter evaluation period is separated by a short reference parameter evaluation period, which is of equal duration. The reference periods are not of sufficient duration to allow the hemodynamic feedback systems to return the hemodynamic system to a substantially equilibrium state and hence are each much shorter than conventional baseline pacing periods. In still another example, a gradient-based approach is employed wherein test parameters are adaptively adjusted based on changes in transient cardiac performance over a sequence of short evaluation periods until some degree of convergence is achieved.

Preferably, the actual measurements of transient cardiac performance are made shortly before and shortly after each change of control parameter. The measurements made before and after each change are compared, and the result is used as a measurement of relative efficacy of the corresponding control parameter values. An optimal control parameter value (or set of values) is derived from the performance comparisons that were made from the set of control parameters values that were tested. The changes in test parameter values are made as rapidly as possible, consistent with obtaining statistically meaningful estimates of cardiac performance.

Parameters to be optimized may include, for example, pacing base rate, maximum and minimum tracking rate, AV delay and interventricular delay and, in general, any interval value such as those employed with four chamber pacing. Furthermore, the techniques of the invention can be exploited to perform simultaneous optimization of multiple parameters, such as the simultaneous optimization of AV delay values and interventricular delay values. Also, the techniques can be used for non-interval optimization as well, such as in the setting of cardiac contractility modulation, wherein a sub-threshold electrical stimulus increases the contractility of the heart.

In one implementation, parameter optimization is performed only in conjunction with an external programmer, i.e. the external programmer transmits test parameters to the implanted device then processes hemodynamic sensor data recorded during the optimization procedure to identify the parameter settings that yield optimal cardiac performance. In other implementations, parameter optimization is performed automatically by the implanted device itself as often as needed, such as following a significant change in patient posture, heart rate, activity level, etc.

In its various implementations, parameter optimization can be performed more rapidly than with predecessor techniques. Other advantages of the invention may be achieved as well. Both system and method embodiments of the invention are set forth.

BRIEF DESCRIPTION OF THE DRAWINGS

Further features and advantages of the present invention may be more readily understood by reference to the following description taken in conjunction with the accompanying drawings, in which:

FIG. 10 is a graph showing AV delay test parameters applied during the test intervals of FIG. 9;

FIG. 11 is a graph showing simulated cardiac performance using the test parameters of FIG. 10;

FIG. 12 is a graph showing pairs of cardiac performance difference values obtained using the test parameters of FIG. 11;

FIG. 13 is a graph showing a curve fitted through the pairs of cardiac performance difference values of FIG. 12 and particularly showing an estimated optimal value of AV delay, which closely approximates the theoretical optimal AV delay shown in FIG. 2;

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
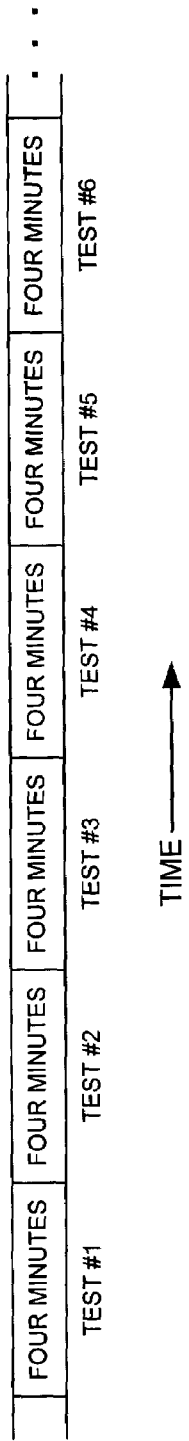
FIG. 1 is a graph showing conventional, long test intervals for achieving control parameter optimization.
Figure 3:
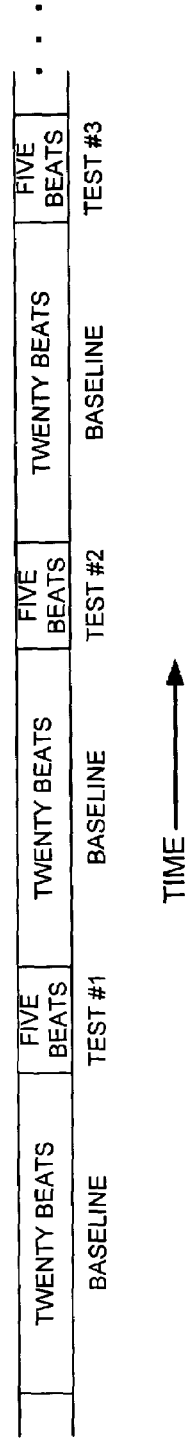
FIG. 3 is a graph showing alternating baseline/test intervals for achieving parameter optimization.
Figure 2:
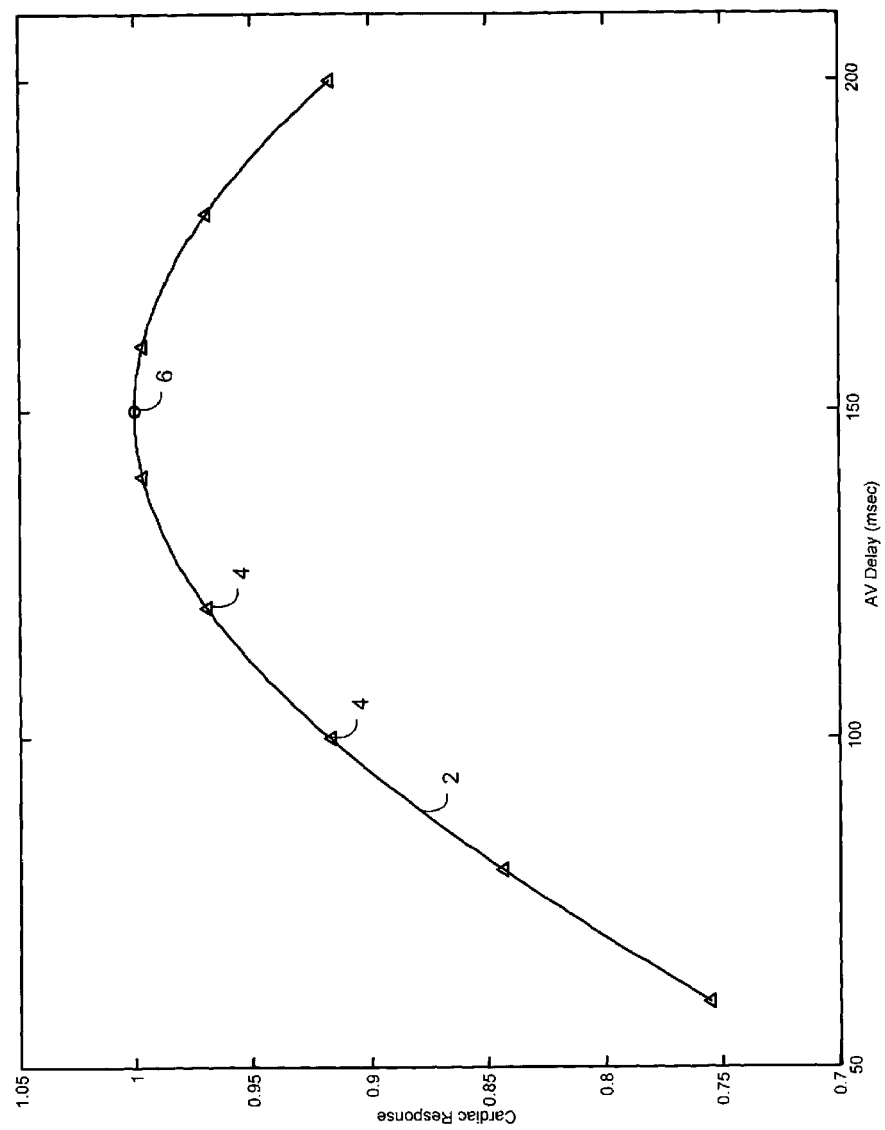
FIG. 2 is a graph showing an exemplary cardiac performance curve varying as a function of AV delay.
Figure 4:
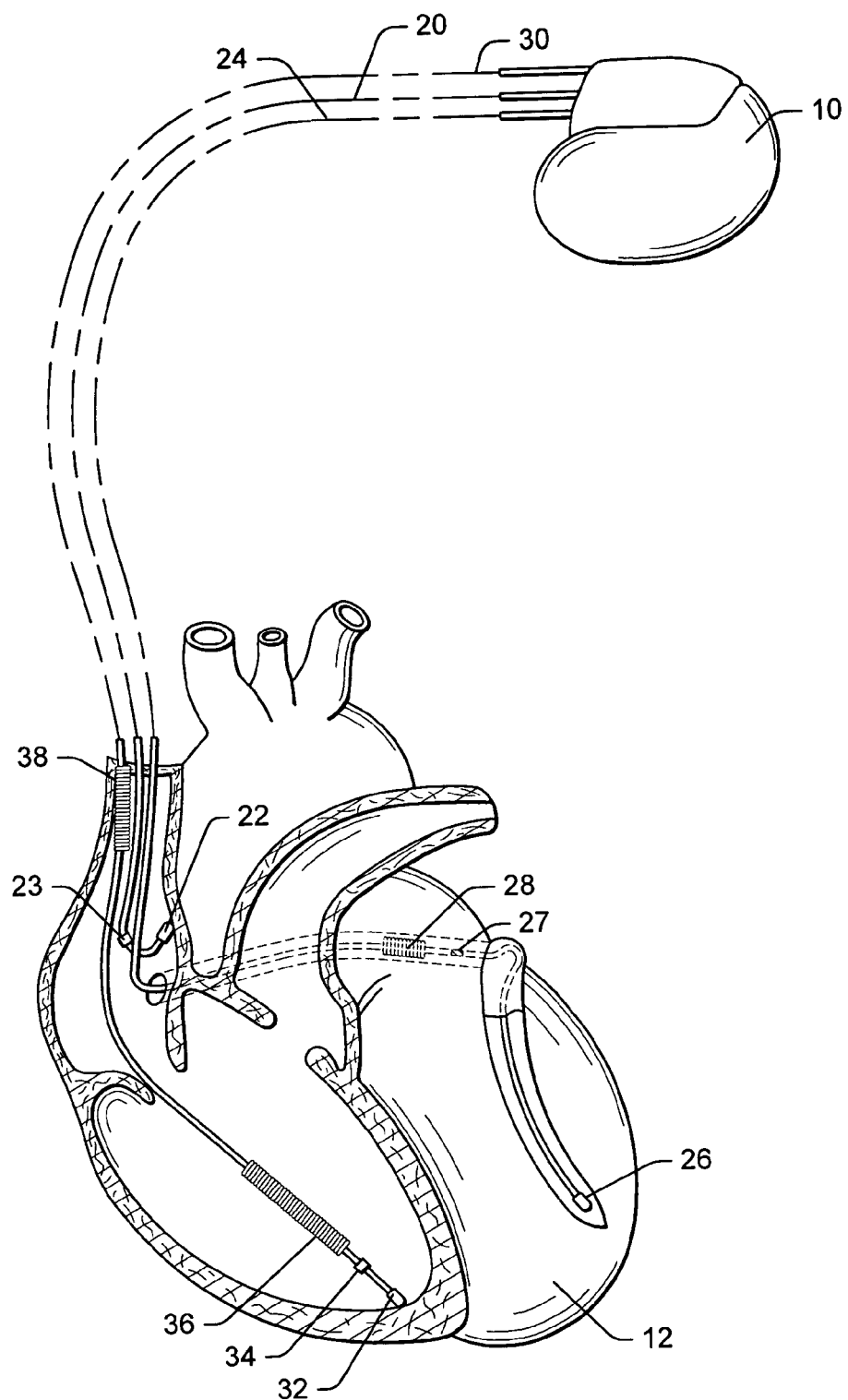
FIG. 4 is a simplified diagram illustrating an implantable stimulation device in electrical communication with at least three leads implanted into a patient's heart for delivering multi-chamber stimulation and shock therapy.

As shown in FIG. 4, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. Although not show, the system of leads may also include one or more RA rings in the proximal coronary sinus, one or more LV rings and an LV coil.

Figure 5:
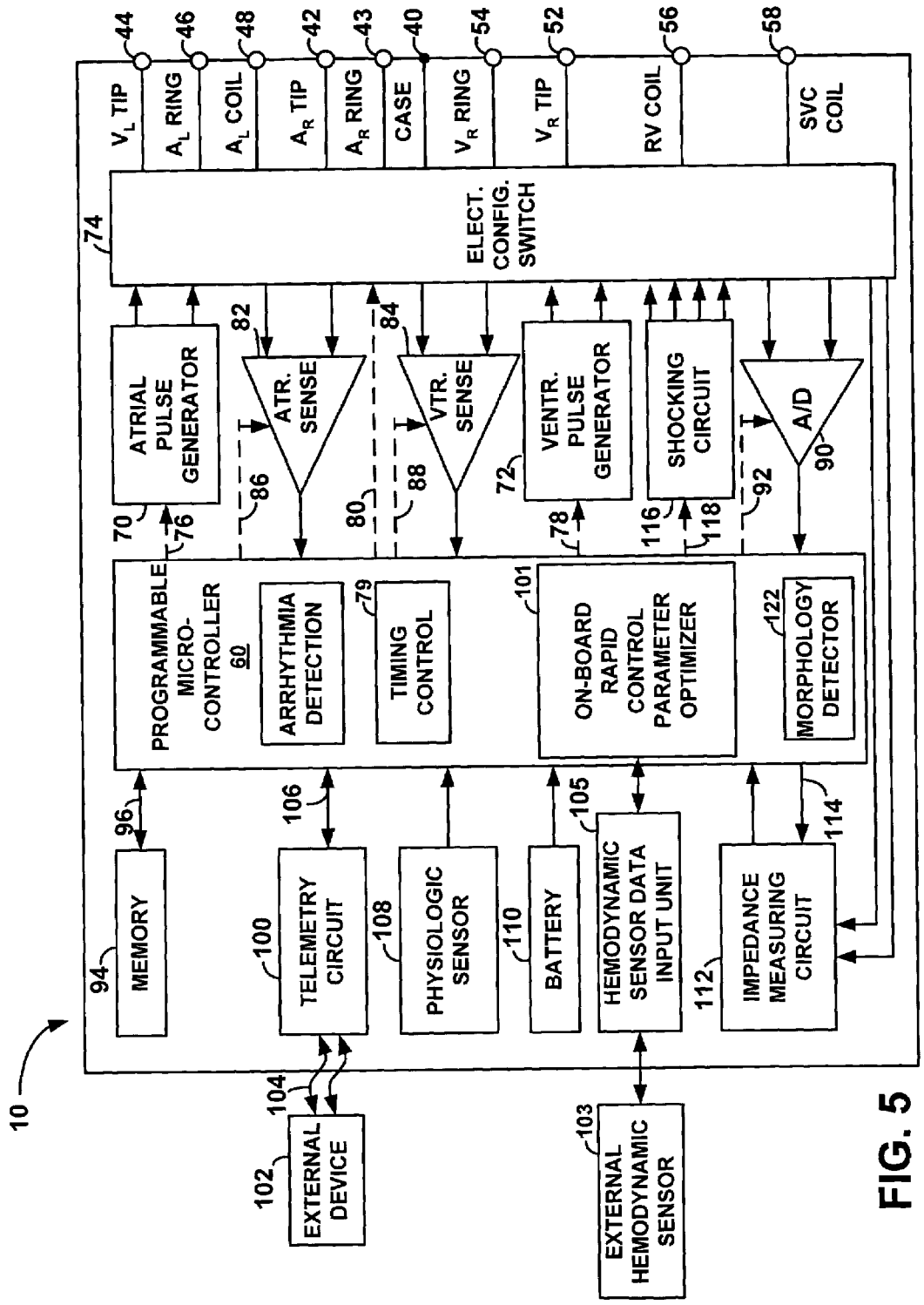
FIG. 5 is a functional block diagram of a multi-chamber implantable stimulation device illustrating the basic elements of a stimulation device, including a pacing parameter optimizer for use in performing rapid pacing parameter optimization.

As illustrated in FIG. 5, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 5, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Additional terminals may be provided for use with RA rings, LV rings or an LV coil.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 5, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, interatrial (RA-LA) interval, or interventricular (RV-LV) interval, etc.) evoked response windows, alert intervals, marker channel timing, etc., which is well known in the art. The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to sense voltages between any of the electrodes of the right atrial lead 20, coronary sinus lead 24, and the right ventricular lead 30, and the can, through the switch 74 for sensing the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), as is known in the art.

Microcontroller 60 includes an on-board rapid control parameter optimizer 101, which operates to rapidly optimize pacing control parameters in accordance with techniques to be described in detail below with reference to FIGS. 7-24. The rapid optimizer uses cardiac performance data received from an implanted hemodynamic sensor 103, which may be but is not necessarily external to the implanted device housing. A wide variety of hemodynamic sensors may be employed alone or in combination for monitoring cardiac performance. Examples include sensors described in U.S. Pat. Nos. 6,575, 912, 6,561,984, 6,527,729, 6,491,639, 6,477,406, and 6,409, 675, each to Turcott and each of which is incorporated by reference herein. Signals from the hemodynamic sensor are input via a hemodynamic sensor data input unit 105.

For arrhythmia detection, the device 10 utilizes cardiac event detection unit to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, LV-RV interval, etc.) at which the atrial and ventricular pulse generators, 70 and 72, generate stimulation pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

The stimulation device additionally includes a battery 110, which provides operating power to all of the circuits shown in FIG. 5. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 5, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules) or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Overview of External Programmer

Figure 6:
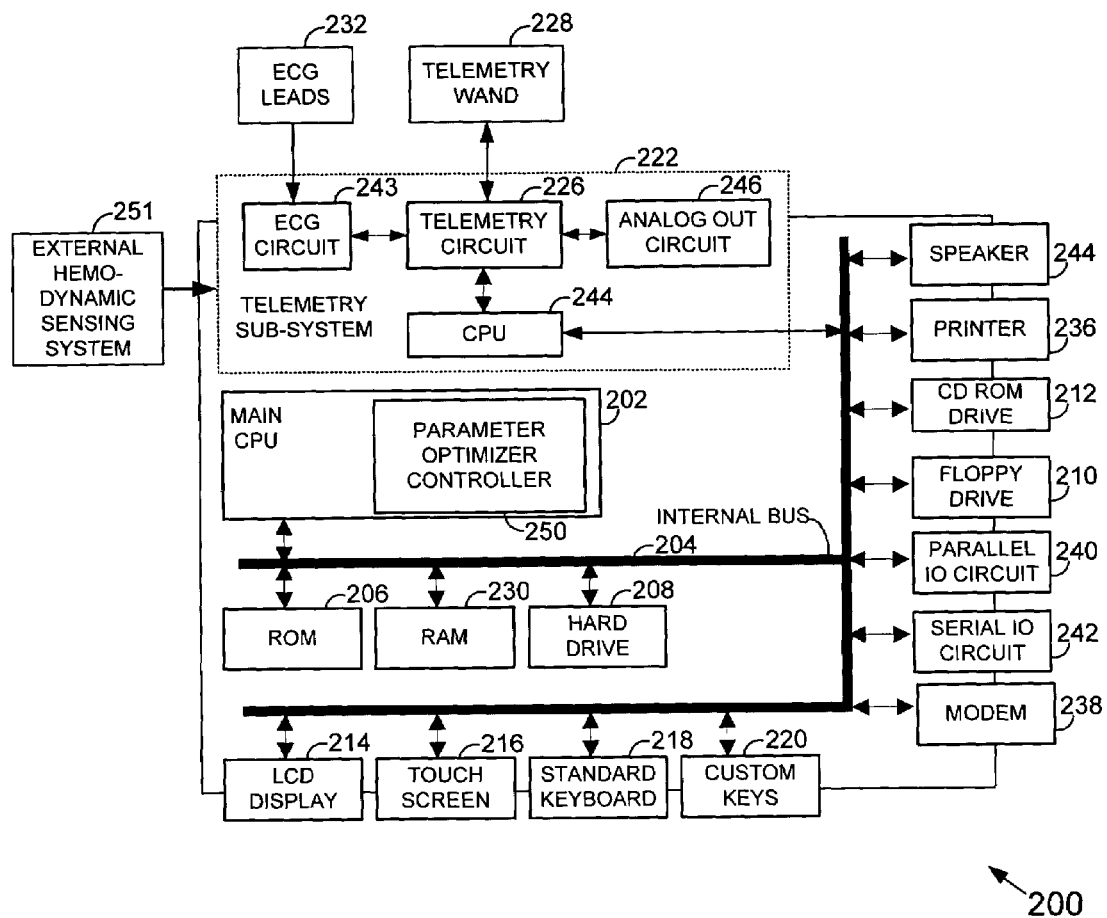
FIG. 6 is a functional block diagram illustrating components of an external programmer for use in programming the implanted device of FIG. 5, including a pacing parameter optimization controller.

FIG. 6 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Depending upon the specific programming of the external programmer, programmer 200 may also be capable of processing and analyzing data received from the implanted device to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210 and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 200 to retrieve data stored within the implanted medical device. To this end, CPU 202 transmits appropriate signals to a telemetry subsystem 222, which provides components for directly interfacing with the implanted device. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient near the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Thus, the programmer receives data both from the implanted device. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Prior to reprogramming specific parameters, the physician may control the external programmer to display any or all of the data retrieved from the implanted device, including displays of IEGMs and statistical patient information. Any or all of the information displayed by programmer may also be printed using a printer 236.

CPU 202 includes a parameter optimizer controller 250 for controlling the optimization of control parameters in coordination with the on-board optimizer 101 of FIG. 5. In one implementation, controller 250 inputs data from an external hemodynamic status sensing system 251, such a Doppler echocardiography system, nuclear imaging system, impedance cardiography system or thermodilution system. The operation of controller 250 in conjunction with the on-board optimizer will be described in further detail below.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided. A speaker 244 is included for providing audible tones to the user, such as a warning beep in the event the physician provides improper input. Telemetry subsystem 222 additionally includes an analog output circuit 246 for controlling the transmission of analog output signals, such as emulated EKG signals output to an EKG machine or chart recorder.

With the programmer configured as shown, a physician or other user operating the external programmer is capable of retrieving, processing and displaying a wide range of information received from the implanted device and to reprogram the implanted device if needed. The descriptions provided herein with respect to FIG. 6 are intended merely to provide an overview of the operation of programmer and are not intended to describe in detail every feature of the hardware and software of the device and is not intended to provide an exhaustive list of the functions performed by the device.

The operations of the implanted device of FIG. 5 and the external programmer of FIG. 6 for rapidly optimizing pacing control parameters will now be described with references to the remaining FIGS., which include various flow-charts. In the flow charts, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device or external programmer. Those skilled in the art may readily write such a control program based on the flow charts and other descriptions presented herein.

Rapid Optimization Under Control of External Programmer

Figure 7:
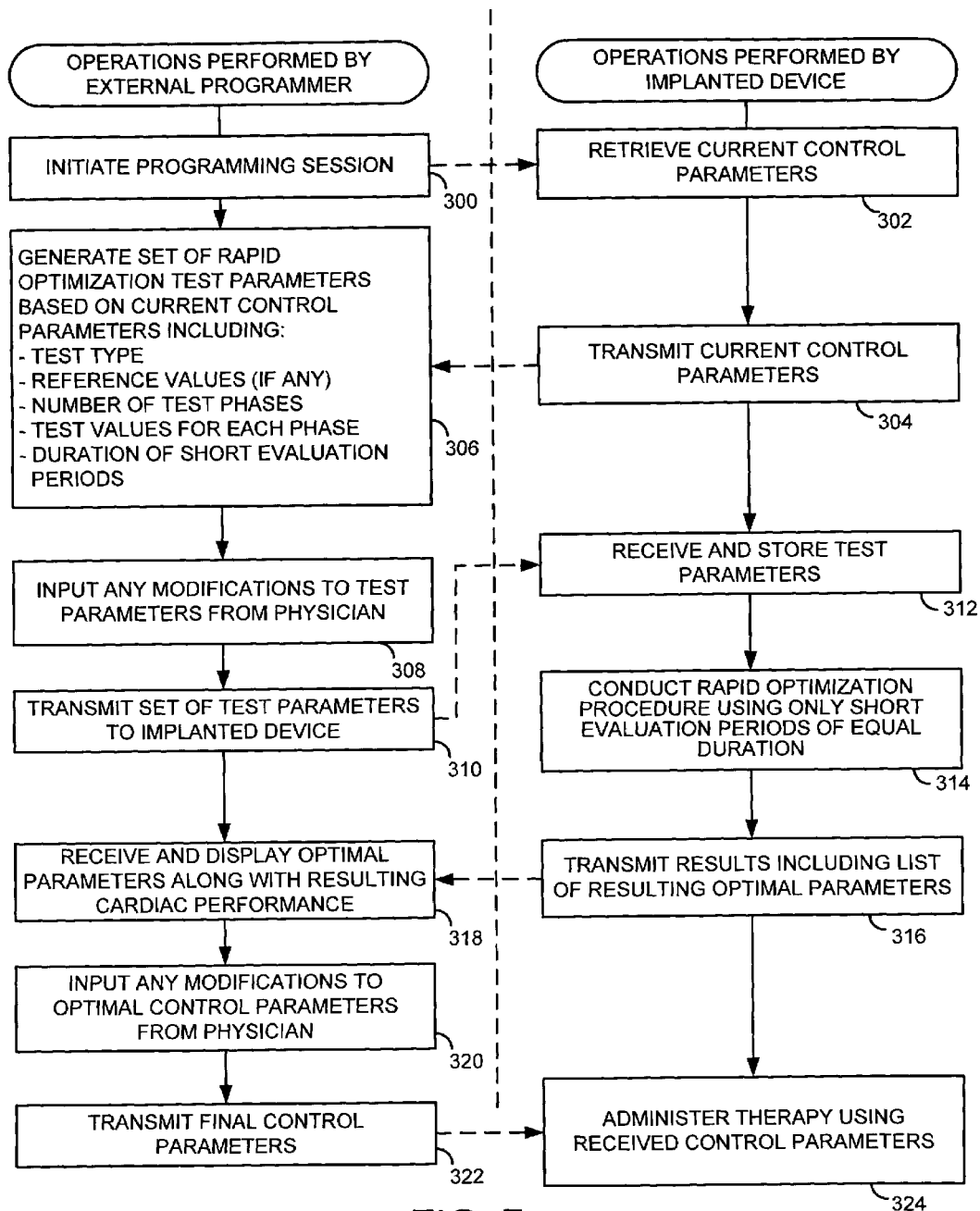
FIG. 7 is a flow chart illustrating an exemplary method performed by both the implanted device of FIG. 5 and the external programmer of FIG. 6 for controlling the rapid optimization of pacing parameters.

Referring to FIG. 7, rapid optimization of pacing control parameters under the control of the external programmer with physician supervision will now be described. The procedure is typically performed during a follow-up session between the patient and physician in the patient's office or during an initial programming session after the device has been implanted. Although the patient is typically present, if transtelephonic monitoring and control is provided, rapid optimization may also be performed under physician supervision while the patient is at home. (Alternatively, as will be explained below, rapid optimization may be automatically performed by the implanted device itself, without direct control by the external programmer.) In any case, steps performed by the external programmer are shown on the left; steps performed by the implanted device are shown on the right.

Initially, at step 300, the physician initiates a rapid optimization programming session by entering appropriate commands into the external programmer, which are transmitted to the implant device. In response, at step 302, the implanted device retrieves the current set of control parameters being used by the device and, at step 304, transmits those control parameters back to the external programmer. At step 306, the current control parameters are displayed and a set of rapid optimization test parameters are automatically generated by the parameter optimizer controller (unit 250 of FIG. 6) of the external programmer based on the current values. In one example, the current control parameters are designated as a reference values and then sets of test parameters are generated based upon the reference values. The test parameters may, for example, represent a range of control parameters bracketing the reference parameter. For example, if the reference parameter represents the AV delay, the test values may specify various delay values that are slightly longer than or slightly shorter than the reference value.

Three exemplary types of rapid optimization are described herein. In a first technique, pacing with test values alternates with pacing with reference values, with each applied for an evaluation period typically lasting between 5 and 12 seconds. In a second technique, no reference values are employed; rather the rapid optimization procedure cycles through a sequence of different test values. In a third technique, a gradient-based technique is employed in which pacing alternates between two sets of test parameters with the test parameters being adaptively adjusted. Herein, the application of a given set of different test parameters or pair of alternating test parameters corresponds to one "test phase". Accordingly, as will be explained more fully below, with the first technique, each test phase includes two evaluation periods—one in which test parameters are applied and one in which reference parameters are applied. With the second technique, each test phase includes only one evaluation period (in which test parameters are applied.) With the third technique, each phase includes six evaluation periods.

In any case, at step 306, the physician specifies the type of test to performed, i.e. reference-based testing, non-reference-based testing or gradient-based testing. The physician may also specify the number of test phases or the number of different sets of test parameters to be employed. A typical reference-based rapid optimization procedure will employ five to ten phases. A typical non-reference-based procedure will employ 15-30 phases. A typical gradient-based test will include 5-10 phases. In any case, at step 306, the set of test values, the type of test, the duration of each short evaluation period, and other pertinent information is displayed for the physician, who may make further modifications, at step 308. Once the physician is satisfied with the set of test parameters to be employed, the parameters are transmitted, at step 310, to the implanted device, which receives and stores the test parameters in memory at step 312.

Then, at step 314, the implanted device conducts a rapid optimization procedure under control of the rapid control parameter optimizer (unit 101 of FIG. 5) while monitoring cardiac performance using, for example, an implanted hemodynamic sensor. Exemplary rapid optimization procedures to be performed at step 314 are described below with reference to FIGS. 8-24. As part of the test, the rapid pacing parameter optimizer of the implant device determines the set of test parameters that achieved the best cardiac performance. The results of the test, including the optimal parameters that had been identified, are then transmitted at step 316 to the external programmer for display at step 318. Alternatively, the raw data generated during optimization procedure may be transmitted to the external programmer, which then determines the optimal pacing parameters based on the raw data. In any case, the physician then has an opportunity to review the optimal parameter that had been identified and can accept the parameters or can enter any modifications at step 320. For example, the physician may determine that, although the particular set of parameters identified by the rapid optimization procedure did indeed achieve the best cardiac performance, an alternate set of control parameters should be employed, which take into account other factors. In any case, the final set of control parameters are transmitted, at step 322, to the implanted device, which then delivers therapy using the received control parameters.

Although not shown in FIG. 7, following step 318, the physician may also control the implanted device to perform additional rapid optimization procedures, perhaps using a different range of test parameters. This may be performed, for example, if the physician is not satisfied with the cardiac performance achieved using the first set of test parameters and believes that an alternate set of test parameters may achieve even better performance. In any case, once the implanted device is programmed with a new set of control parameters, the patient is sent home and months later, another follow-up session may be arranged so that the control parameters may be optimized again.

By using rapid optimization, individual test parameters can typically be tested within 5 to 12 seconds such that an entire range of test parameters may be tested within only a minute or two. This reduces the amount of time required to optimize control parameters as compared with predecessor techniques. By saving time within each test phase, either the overall optimization process can be reduced in time or more sets of test parameters can be tested with the same period of time. For example, rather than optimize cardiac performance using just a few sets of relatively widely-spaced parameter values, rapid optimization may be performed using a greater number of more closely-spaced parameter settings, thus providing more precise optimization. In other words, the control parameters of the implanted device can be much more finely tuned.

Often, a number of different control parameters may need to be optimized. For example, during a first optimization procedure, the physician can control the external programmer to initiate optimization of AV delay value. During a second phase of the overall optimization process, the physician can control the external programmer to optimize the base pacing rate, and so on. The physician may specify the order with which various parameters are to be optimized. Alternatively, a single optimization procedure may be performed that simultaneously determines optimal values for a set of pacing parameters. This may be achieved by transmitting an entire set of test parameters with varying AV delay values, base rate values, and so on. During the rapid optimization procedure of step 314, the implanted device cycles through various combinations of values to determine the combination of values that achieves the best cardiac performance. In other words, rather than simply determining the optimal AV delay for a given base rate, the implanted device identifies the combination of base rate and AV delay values that achieves the optimal cardiac performance. As appreciated, by ensuring that each individual phase of the test is quite short, this type of "multidimensional" parameter optimization may be much more rapidly performed.

Also, as noted, rather than using a predetermined set of parameter values, the implanted device can be programmed to adaptively select or adjust the values during the test based upon resulting cardiac performance. As the device cycles through a set of parameter values, the rapid optimizer identifies the value that initially achieves the best performance, then increments the parameter in the vicinity of that value. In this manner, the rapid optimizer quickly and adaptively fine-tunes the parameter to achieve optimal cardiac performance.

Referring now to FIGS. 8-24, various strategies for performing rapid optimization procedures will now be described.

Rapid Optimization Using Reference Values

Figure 8:
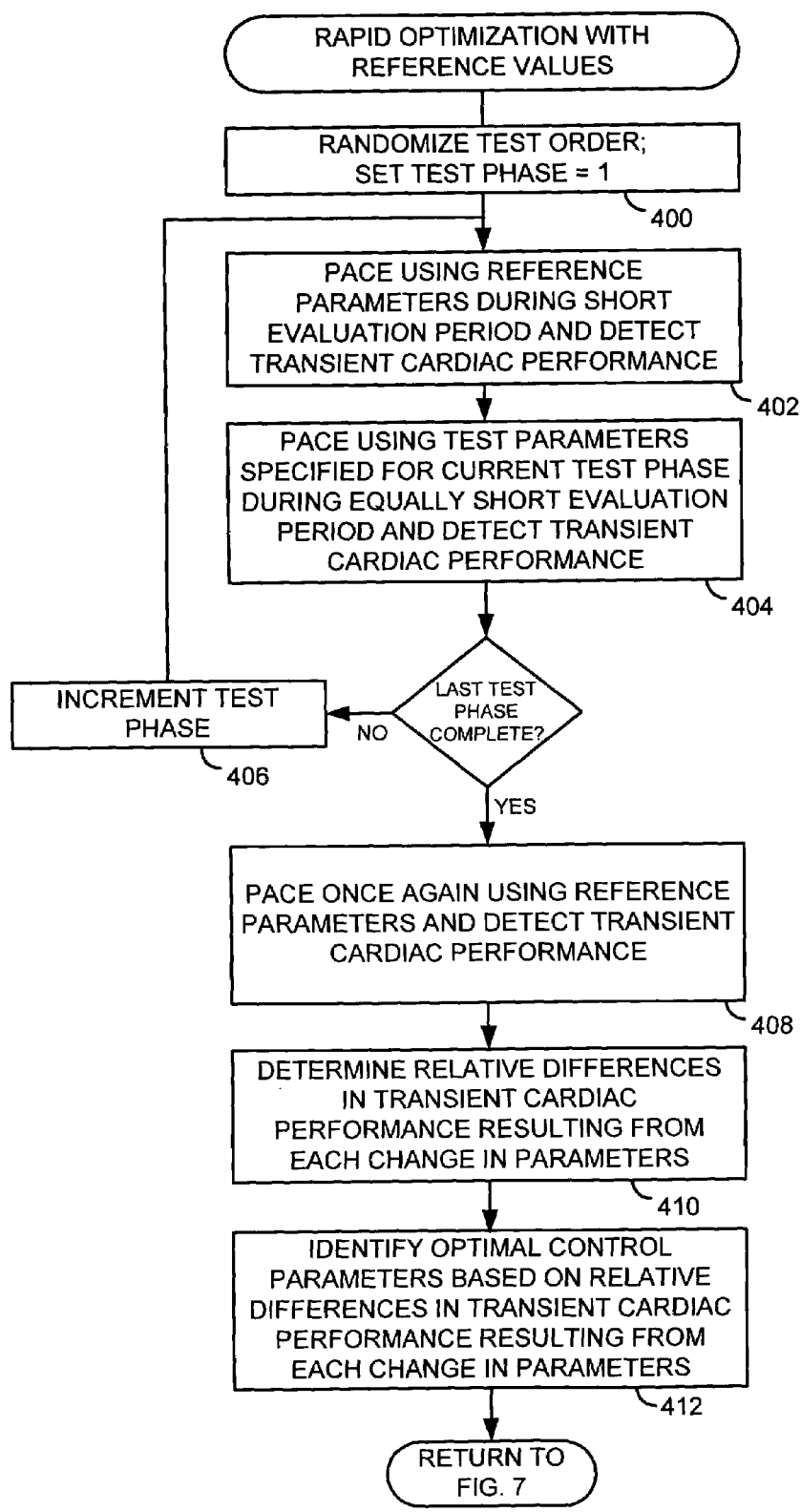
FIG. 8 is a flow chart illustrating a first rapid optimization technique performed by the implanted device of FIG. 5, which employs the use of baseline pacing parameters.
Figure 9:
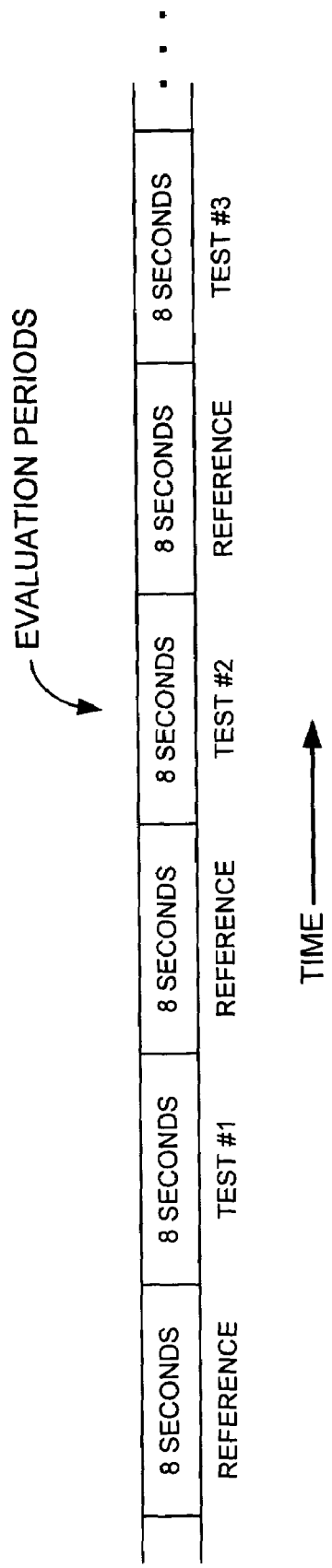
FIG. 9 is a graph showing test intervals for achieving rapid parameter optimization using baseline parameters.

Rapid optimization using reference values will now be described with reference to FIGS. 8-13. At step 400 of FIG. 8, a test_phase designator is set to 1 so as to indicate the first test phase. Also, the test parameters that have already been specified are arranged in random or pseudorandom order to help reduce systemic bias. In other words, if a list of individual AV delay values have been specified, the order of the list is randomized so that the AV delay values will be applied randomly during the test. This will be discussed in greater detail below. Then, beginning at step 402, the implanted device paces the heart of the patient using reference parameters received from the external programmer while monitoring and recording cardiac performance. Reference pacing is performed for the predetermined evaluation period. In the example of FIG. 9, pacing using reference values is performed for an evaluation period of eight seconds. Then, at step 404, the implanted device paces the heart using a first set of test parameters from the randomized list while monitoring and recording cardiac performance. Again, pacing proceeds for the duration of time specified by the parameters received from external device. Typically, the amount of time is equal to the reference period of time, though this is not necessary. In example of FIG. 9, pacing using the first set of test parameters is also performed for only eight seconds.

As noted, a wide variety of hemodynamic sensors may be employed alone or in combination for monitoring cardiac performance. Examples include sensors for detecting values representative of one or more of: stroke volume, cardiac output, end-diastolic volume, end-systolic volume, ejection fraction, cardiac output index, flow through the mitral valve, maximum rate of change of aortic pressure with left ventricular pressure, maximum rate of change of aortic pressure with time (max dP/dt), mean arterial pressure, arterial pulse pressure, vascular volume, and vascular photoplethysmography. Currently, vascular photoplethysmography may be the preferred technique.

If multiple hemodynamic sensors are provided, the values from different sensors may be averaged or otherwise combined to generate a single value representative of overall cardiac performance. Also, an external hemodynamic sensing system may be employed to evaluate hemodynamic performance of the patient. If so, then the determination of the set of parameters achieving optimal cardiac performance is performed by the external programmer based upon data received from the external hemodynamic sensor in combination with data received from the implanted device.

Returning again to FIG. 8, assuming that additional test phases are specified, then the test_phase value is incremented at step 406 and steps 402-404 are performed for the second set of test parameters from the randomized list. Steps 402-404 are repeated until all sets of test parameters have been used. Typically, rapid optimization is performed using 5-10 test phases. In any case, once the last test phase has been completed, step 408 is performed wherein one final phase of reference pacing is performed (which, as explained below, is provided to allow for a final difference value to be calculated.)

Then, at step 410, the implanted device determines differences in hemodynamic performance resulting from each change in pacing parameters performed during the test, i.e. a difference value is calculated for each change from the reference value to a test value and for each change from a test value back to the reference value. This may be achieved by averaging the recorded values of cardiac performance during a short period of time before and after each change in the pacing parameter value then calculating the difference between the averaged values. In one example, the amount of time over which the cardiac performance is averaged is set equal to one respiratory cycle with one second of data following each parameter change excluded. Preferably, each evaluation period is initially set long enough so that it will likely include at least one full respiratory cycle. Data is collected and retrospectively analyzed to identify the respiratory cycles and then "analysis intervals" are defined based on the respiratory cycle. Alternatively, the respiration rate of the patient is directly monitored during the test and used to set the period of time over which the cardiac performance is averaged. In any case, the difference in average cardiac performance is then calculated for each change in pacing parameters. If the transition is from reference value to test value, the sign of the difference is retained. However, if the transition is from test value to reference value, the sign is reversed (i.e. positive to negative or vice versa). In the example of FIG. 8, the difference values are calculated after the test has been completed based on recorded cardiac performance values. Alternatively, the difference values may be calculated during the test, immediately following each change in the value of the parameter being optimized.

Finally, at step 412, the implanted device identifies the test parameter value achieving the best cardiac performance based, for example, on the calculated differences in cardiac performance. More details regarding techniques for identifying the optimal test parameter value are described below. As noted, this calculated optimal value is relayed to the external programmer for review the physician before the implanted device is finally programmed with new reference values.

Note that no requirements are imposed during the optimization procedure that the cardiovascular system be in a particular state of equilibrium. Rather, the change in cardiac performance as the AV delay is switched from one value to another is recognized to contain the essential information, regardless of what, if any, state of hemodynamic equilibrium the cardiovascular system happens to be in.

Simulated test results are illustrated in FIGS. 10-13, for an example wherein AV delay is optimized. As shown in FIG. 10, AV delay values alternate every 8 seconds between a reference value of 130 ms and various test values. The test values are 60 ms, 80 ms, 100 ms, 120 ms, 140 ms, 160 ms, 180 ms and 200 ms, which are employed in a random or pseudorandom order. FIG. 11 shows a simulated cardiac performance as a function of time throughout the test. As can be seen, the cardiac performance does not have time to equilibrate as in conventional optimization procedures wherein the heart is paced with a set of parameters for several minutes. Note that, to simulate noise and measurement variability in the cardiac performance, zero-mean white Gaussian noise with standard deviation equal to 0.5 was added to a simulated true cardiac performance curve. The resulting time series was low pass filtered at 1 Hz. Although simulated, it is believed that the cardiac performance shown in FIG. 11 (and other similar figures discussed herein) fairly represent the sort of cardiac performance expected to be encountered in actual use.

Exemplary difference values 414 are shown in FIG. 12, which were calculated based on the simulated data of FIGS. 10 and 11. As can be seen, a pair of difference values is provided at each test value of the AV delay. A pair of values are provided because, for each test value, two separate difference values are calculated—one based on the transition from the preceding reference value to the test value and one based on the transition from the test value to the subsequent reference value. (The final reference pacing phase of step 408 ensured that each test value has a pair of corresponding difference values.)

A curve 416 (shown in FIG. 13) is fitted through the pairs of points using a curve fitting technique, then the AV delay achieving the optimal cardiac performance is determined based on the curve. In the example of FIG. 13, a $3^{rd}$ degree polynomial was fit to the data, but any continuous function that supports a monomodal shape could be used. Using a fitting function with fewer parameters than the number of test values is desirable as that results in an averaging over the measured data points, even those occurring at different test parameter values. This desirable attribute typically diminishes as the number of parameters increases. For example, piecewise-linear interpolation would typically confer no advantage over simple averaging of the measures for each test parameter and selecting as optimum the test parameter associated with the largest average.

In FIG. 13, the calculated optimal AV delay is marked by "x" 418. The actual optimal AV delay is marked by circle 420. As can be seen, the calculated optimal AV delay is very close to the actual optimal AV delay. Indeed, there is little or no difference in the hemodynamic performance between actual optimal value and the calculated optimal value. Note that the final reference pacing phase (step 408) need not necessarily be performed. If omitted, then one of the test values will have only a single corresponding difference value rather than a pair of difference values but this will not likely significantly affect the resulting curve and hence will not significantly affect the resulting calculated optimal AV value. Indeed, as will be explained below, reference pacing phases need not be performed at all. Also, it is not necessary that all AV delay values within the initially determined range need be applied. Rather, a subset of values is often sufficient. In the example, of FIGS. 10-13, if only every other AD delay value was instead used, a suitable approximation for the optimal AV delay value would nevertheless be obtained. Moreover, note that, for the example of FIGS. 10-13, the order of the AV test parameters is random. However, alternatively, the parameters may be incremented through a range of values from low to high (or from high to low) though this might introduce bias and hence random ordering is preferred.

Also, the technique can be repeatedly applied, with the initial iteration having a very broad set of test values, such as the AV delay range of 60 ms-200 ms of FIG. 10, and with each successive iteration having a progressively narrower range. There are two advantages of this. One is that if there is a dependence of the optimum control parameter value on the underlying hemodynamic state, the iterative approach allows the estimated optimum to track the true optimum as the cardiovascular system equilibrates and stabilizes, without sacrificing the rapidity of optimization as with conventional techniques. The second advantage is that the system can rapidly track changes in the underlying true optimum parameter value due to external factors such as change in body posture or autonomic tone.

Thus FIGS. 8-13 illustrate that a very accurate estimate of the optimal AV delay value can be achieved using the method of the invention based on only a short optimization procedure. In the example, an entire optimization procedure based on eight different test values of AV delay values lasts only 136 seconds (or less than 2½ minutes) and yet achieves accurate results.

Rapid Optimization Without Reference Values

With reference to FIGS. 14-19, the non-reference-based technique is set forth. The technique is similar to that of FIGS. 8-13 and only pertinent differences will be described in detail. At step 460, the implanted device initially sets the test_phase indicator to 1 and the list of test parameters is randomized. Thereafter, rather than pacing the heart using reference values, the device immediately proceeds to step 462 wherein the heart is paced using the first set of test parameters while cardiac performance is monitored and recorded. The test_phase indicator is incremented, step 464, until the last phase has been completed. Then, at step 466, the device again paces the heart using the first value of the test parameter (i.e. the parameter of test phase 1) while again monitoring cardiac performance. At step 468, the implanted device determines differences in cardiac performance resulting from each change in pacing parameters performed during the test. As before, this may be achieved by averaging the recorded values of cardiac performance during a short period of time (preferably set equal to one respiratory cycle) before and after each change in the pacing parameter value (while excluding one second of data after each transition) then calculating the difference between the averaged values.

Each transition results in a single difference value associated with the transition. The single difference value is recorded twice—once in connection with the before-transition parameter value and once in connection with the after-transition parameter value. Thus, for a test using eight values of the AV delay, a total of fifty-six difference values are typically recorded at step 468, i.e. seven values are recorded for each particular value of the AV delay with the seven values representing transitions to (or from) the other seven values. When recording the difference value for a given test parameter value, if the transition was from a previous test value to the given test value, the sign of the difference is retained. However, if the transition is from given test value to a subsequent test value, the sign is reversed (i.e. positive to negative or vice versa). Again the difference values may be calculated after the test has been completed based on recorded cardiac performance values or may be calculated during the test, immediately following each change in the value of the parameter being optimized. Then, at step 470, the implanted device identifies the parameter value achieving the best cardiac performance based on an analysis of the difference values.

Figure 14:
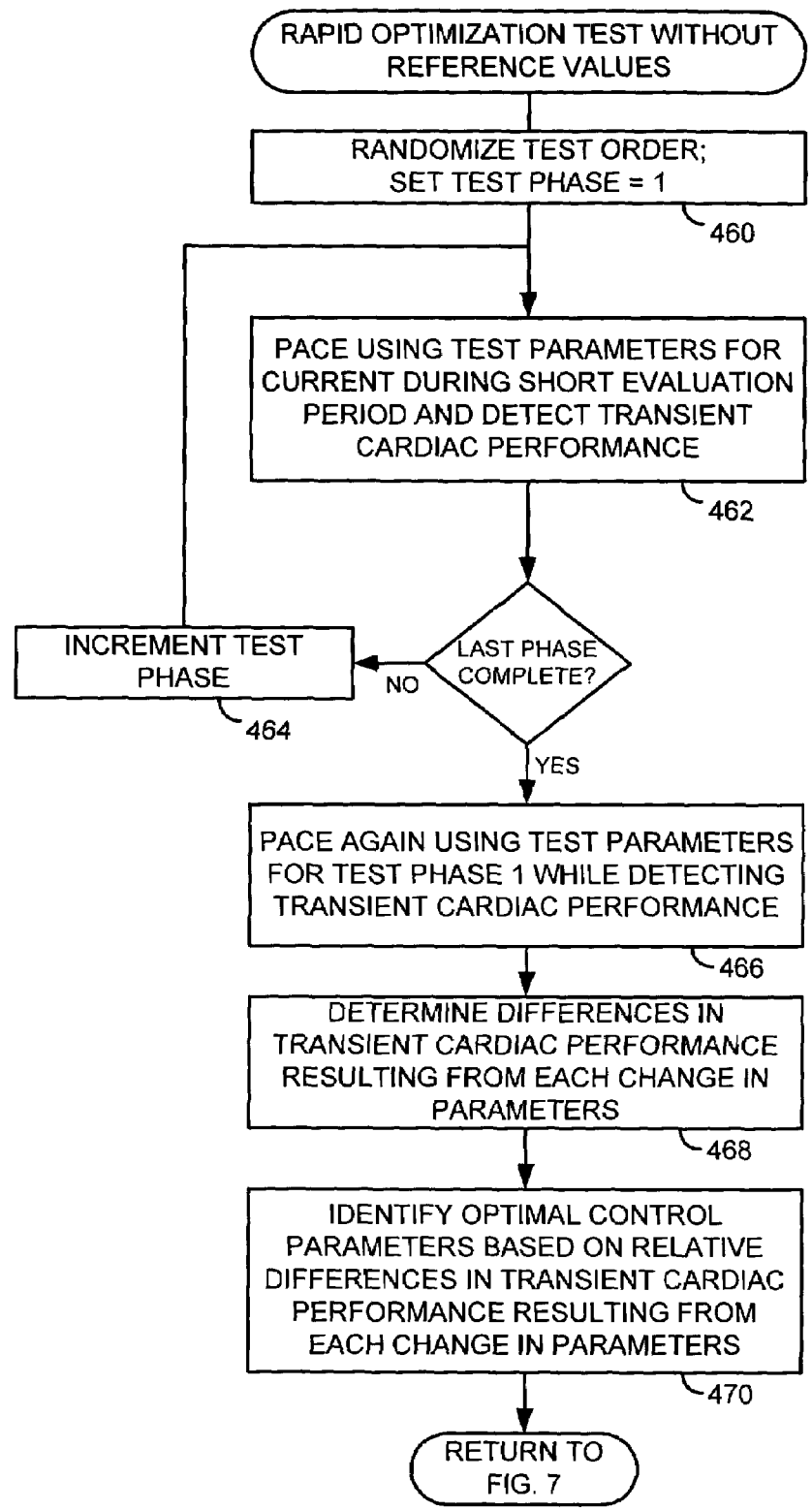
FIG. 14 is a flow chart illustrating a second rapid optimization technique performed by the implanted device of FIG. 5, which does not employ baseline pacing parameters.
Figure 15:
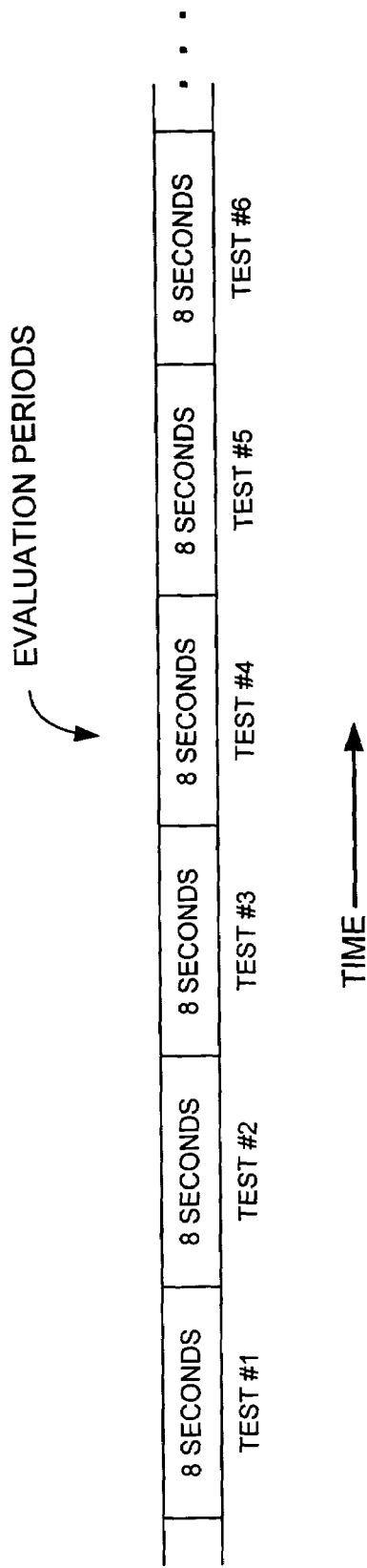
FIG. 15 is a graph showing test intervals for achieving rapid parameter optimization without using baseline parameters.
Figure 16:
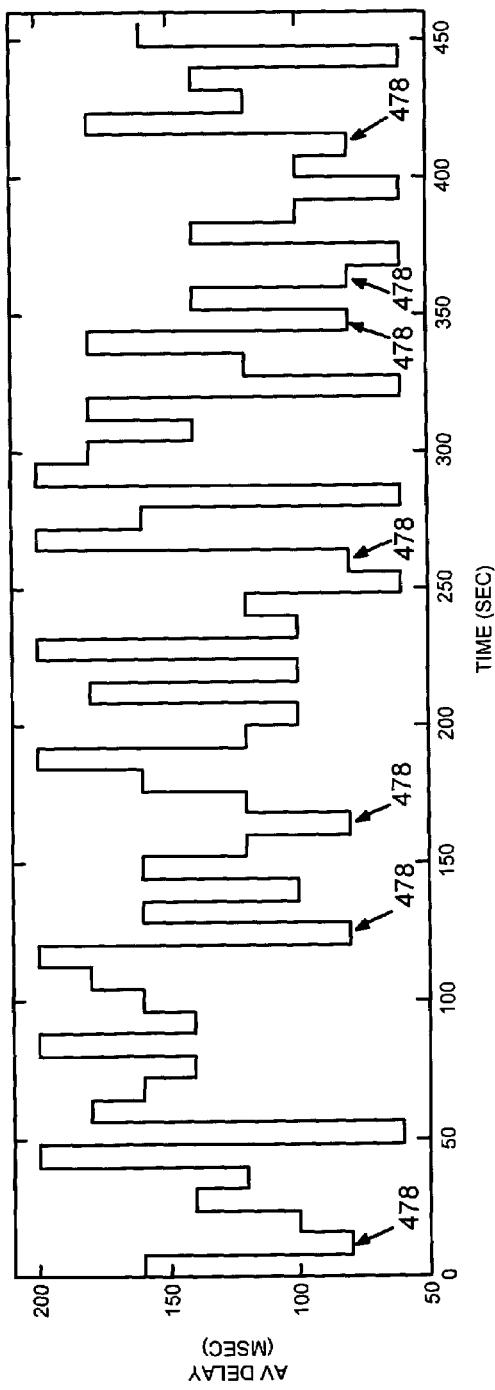
FIG. 16 is a graph showing AV delay test parameters applied during the test intervals of FIG. 15.

FIG. 15 illustrates the procedure of FIG. 14 wherein pacing is performed without reference values. Simulated test results are illustrated in FIGS. 16-19, for an example wherein AV delay is optimized. As shown in FIG. 16, a given AV delay value is employed for eight seconds then a switch is automatically made to another one of the AV delay values. Again, the test values are 60 ms, 80 ms, 100 ms, 120 ms, 140 ms, 160 ms, 180 ms and 200 ms. In this example, the randomized test values are cycled so that all of the possible transitions between individual test values are generated. Hence, a total of fifty-seven phases are employed, each lasting eight seconds, with each of the fifty-six possible transitions from one parameter setting to another being invoked at some point during the test. However, as before, it is not necessary that all AV delay values within the initially determined range need be applied. Rather, a subset of values is often sufficient. For example, if only every other AD delay value was instead used, a suitable approximation for the optimal AV delay value would nevertheless be obtained.

FIG. 11 shows simulated cardiac performance as a function of time throughout the test. As before, the cardiac performance does not have time to equilibrate as in conventional optimization procedures wherein the heart is paced with a set of parameters for several minutes. Again, to simulate noise and measurement variability in the cardiac performance, zero-mean white Gaussian noise with standard deviation equal to 0.5 was added to a simulated true cardiac performance and the resulting time series was low pass filtered at 1 Hz.

Figure 17:
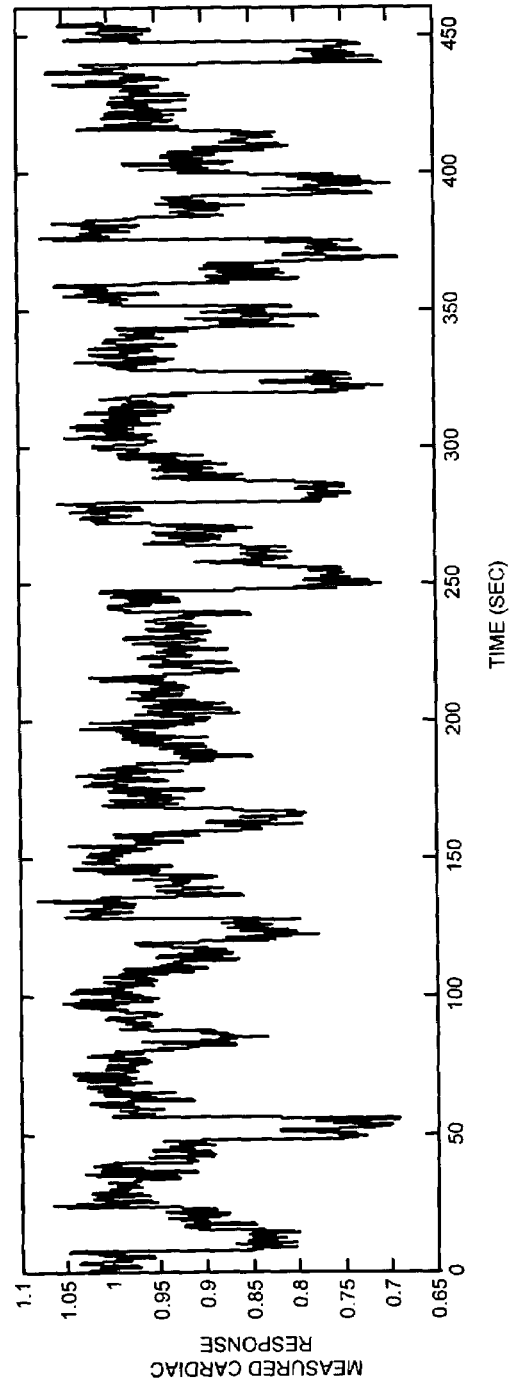
FIG. 17 is a graph showing simulated cardiac performance using the test parameters of FIG. 16.
Figure 18:
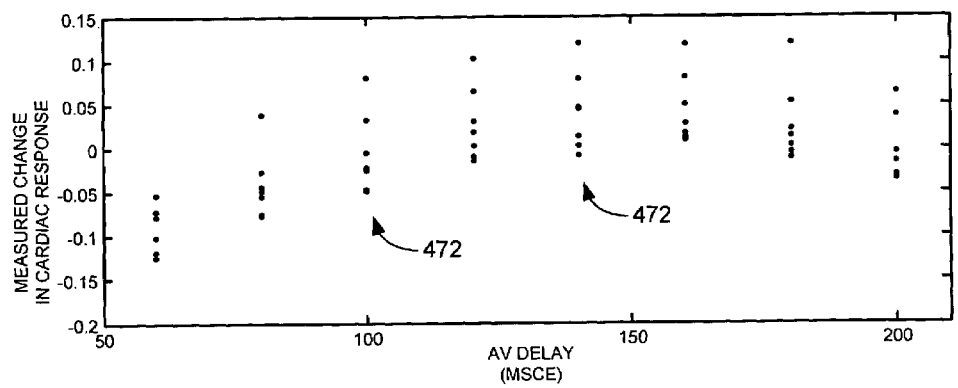
FIG. 18 is a graph showing a set of cardiac performance difference values obtained using the test parameters of FIG. 16.

Exemplary difference values 472 are shown in FIG. 18, calculated based on the simulated data of FIGS. 16 and 17. Seven difference values are recorded at each test value of the AV delay. (In some cases, the difference values are nearly identical and hence are superimposed on one another on the plot of FIG. 18 and so are not separately visible.) Seven difference values are recorded for each test value because, as explained, each possible transition between the eight test values is generated during the test. (The final pacing phase of step 466 ensures that each test value has seven corresponding difference values.)

Figure 19:
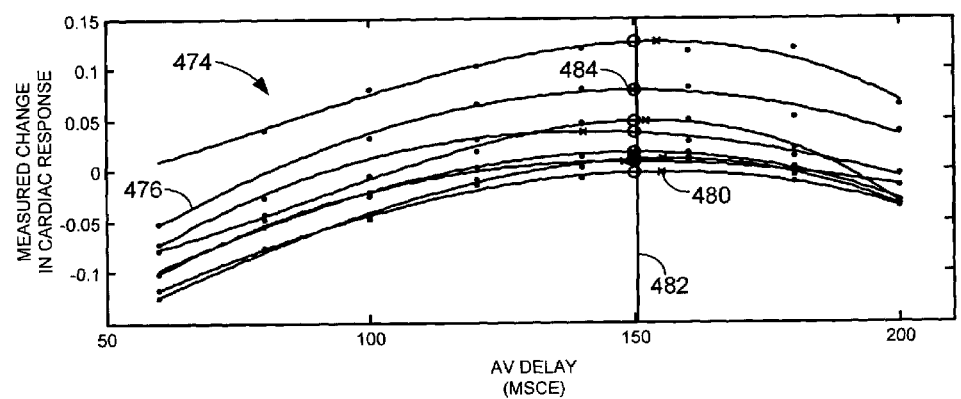
FIG. 19 is a graph showing a curve fitted through the set of cardiac performance difference values of FIG. 18 and particularly showing an estimated optimal value of AV delay, which closely approximates the theoretical optimal AV delay shown in FIG. 2.

As before, a single curve may be fitted to all data points, then the optimal AV delay calculated based on that curve. However, in the example of FIG. 19, eight individual curves 474 are fitted through the points. Each individual curve is fitted through points sharing a common before-transition AV delay value. For example, curve 476 is based on points wherein 80 ms was the before-transition value. The corresponding phases are identified in FIG. 16 by reference numerals 478. Then, an optimal AV delay value is estimated for each of the eight individual curves and then the eight estimates are averaged together to yield a final estimate for the optimal AV delay. In FIG. 19, the individual estimates of the AV delay are marked by "x"s 480. The average of the individual estimates is marked by vertical line 482. The actual optimal AD delay value is identified by circles 484. As can be seen, the calculated optimal AV delay is again very close to the actual optimal AV delay and there is little or no difference in the hemodynamic performance between actual optimal value and the calculated optimal value. Also, as before, the final pacing phase (step 466) need not necessarily be performed.

In general, with N test parameter values, in order to test all possible differences N×(N−1) comparisons will be needed, which requires N×(N−1)+1 test phases. This is the approach used in the present example to simplify the illustration of the concept. In practice, many fewer comparisons can be made without significantly degrading the estimation of the optimum value. One approach is to list the N test values a small number of times (e.g., N/2 times), with N typically 6-8. The order is then randomized, and the analysis is performed as in the example, or, rather than fitting a single polynomial for each before-transition value, a single polynomial is fit to the entire set of differences. Interpolation and averaging compensate for the missing data points. Alternatively, N can be made small, e.g., 4 rather than 8, and all possible comparisons performed.

Thus, although an example is described wherein all possible transitions from one test value to another are generated at some point during the test, this is not necessary and only a sub-set of the total number of transitions may instead be used. Routine experimentation can be performed to determine the minimum number of actual transitions required to still obtain a suitably accurate estimate of the optimal pacing parameter within typical patients. As can be appreciated, there is a trade-off between the accuracy with which the optimal value is determined and the number of test phases required to achieve that level of accuracy.

Thus FIGS. 14-19 illustrate that a very accurate estimate of the optimal AV delay value can be achieved without the use of a reference value. In the example, because all possible transitions are generated, the entire AV optimization procedure lasts 7½ minutes. More rapid optimization may be achieved by reducing the total number of transitions. Although typically not as fast as the reference-based technique of FIGS. 8-13 when all possible parameter transitions are exploited, since reference phases are not employed and since all possible transitions need not be evaluated, the non-reference-based technique can typically provide equally precise estimates in less time than the reference-based technique or can provide more precise estimates in the same amount of time. Also, the non-reference technique has advantages in circumstances wherein there is no a priori information indicating an appropriate reference value to be used. Hence, in some implementations, the non-reference technique may be preferred during an initial post-implant optimization procedure to identify an optimal parameter value to be used as an initial reference value. Thereafter, the reference-based technique may be preferred for use in adjusting the reference value.

Rapid Optimization Using Gradient Technique

Figure 20:
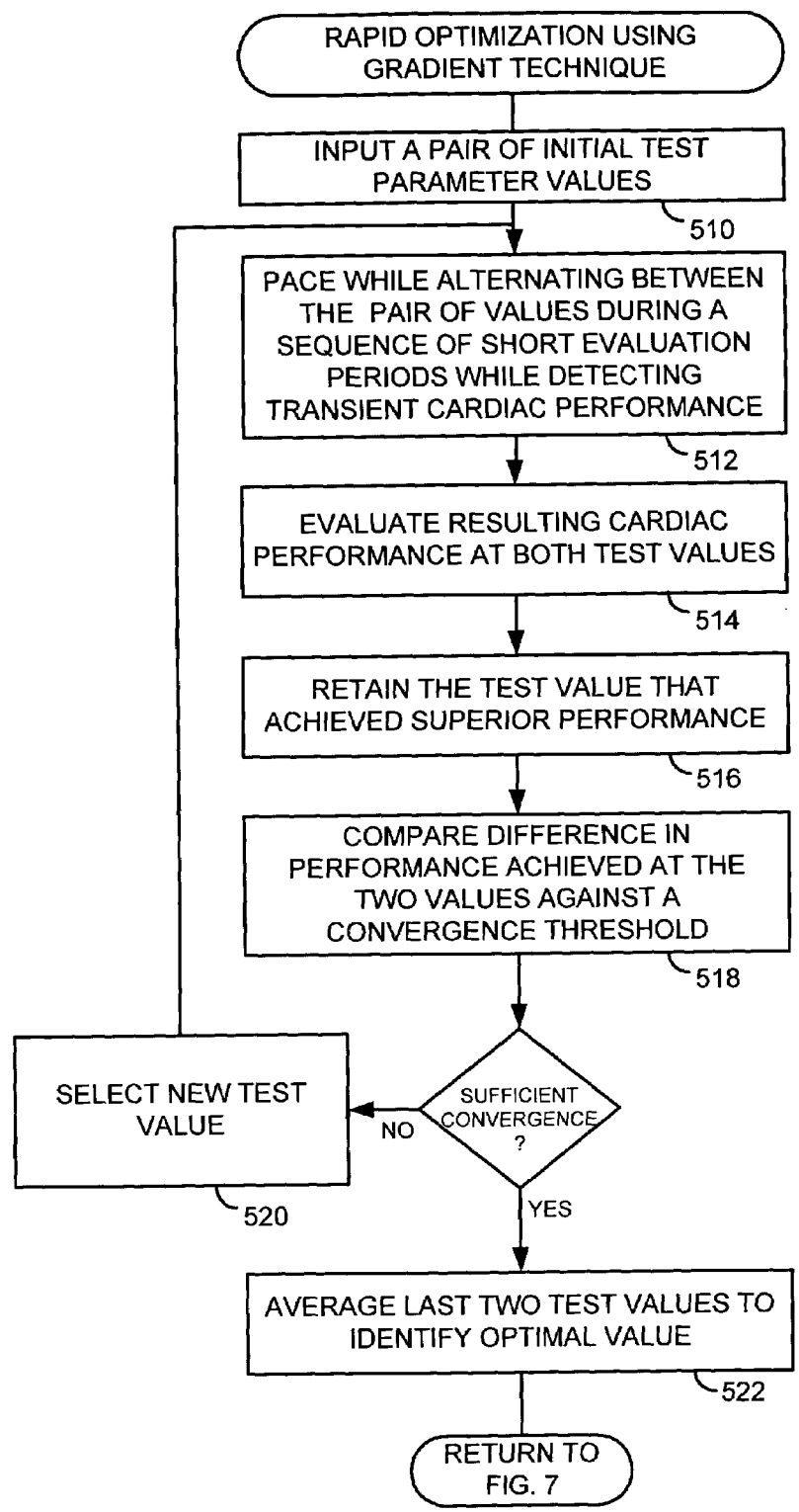
FIG. 20 is a flow chart illustrating a third rapid optimization technique performed by the implanted device of FIG. 5, wherein test phase durations are adaptively set based on ongoing changes in cardiac performance.
Figure 21:
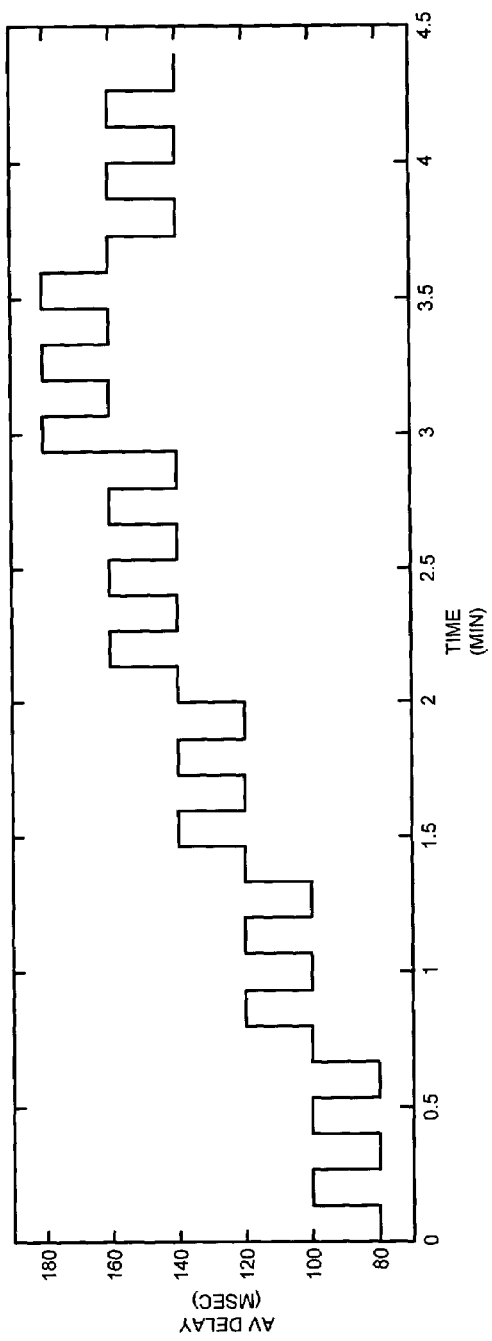
FIG. 21 is a graph showing AV delay test parameters applied during the adaptive method of FIG. 20.

With reference to FIGS. 20-21, a gradient-based or adaptive technique for estimating an optimal pacing parameter is described. Initially, at step 510, a pair of initial values of pacing parameters to be optimized is input from an external programmer, such as AV delay values of 80 ms and 100 ms. At step 512, the implanted device then paces the heart while alternating between the pair of values during a sequence short evaluation periods, i.e. the device paces the heart using one of the values for one test phase (typically 5-12 seconds) then switches to the other value for the next test phase then switches back. After alternating for several test phases (typically six total phases), the device, at step 514, evaluates the average cardiac performance achieved at each test value. This may be accomplished, for example, by averaging the cardiac performance during the last few seconds of each test phase wherein a particular test value was employed. As before, the period of time over which cardiac performance is averaged is preferably set equal to one respiratory cycle. At step 516, the device then compares the resulting cardiac performance for the two parameter settings and selects the parameter setting that achieved superior performance for use in further optimization. At step 518, the device also calculates an absolute value of a difference between the two averaged cardiac performance values and compares it against a predetermined convergence threshold. Assuming the difference exceeds the convergence threshold, the device then selects a new value of the pacing parameter at step 520 and repeats steps 512-528 using the new value and the previously retained value. Again, after several test phases where the device alternates between the two values, the device selects the value yielding the superior performance. Eventually, a pair of values will be tested wherein there is little or no difference in resulting cardiac performance. As such, the absolute value of the difference in cardiac performance calculated at step 518 will fall below the convergence threshold and the test will be complete. An average of the two final parameter settings is then calculated at step 522 for use as a new reference value for further pacing.

Routine experimentation may be employed to identify a suitable value for the convergence threshold to be used with each pacing parameter to be optimized, which is sufficiently small to ensure that premature convergence is not improperly detected and yet sufficiently large so that the optimization procedure eventually settles on a optimal parameter setting and does not merely oscillate between two pairs of parameter values. Also, some fixed maximum number of test phases may be imposed to ensure finality.

Figure 22:
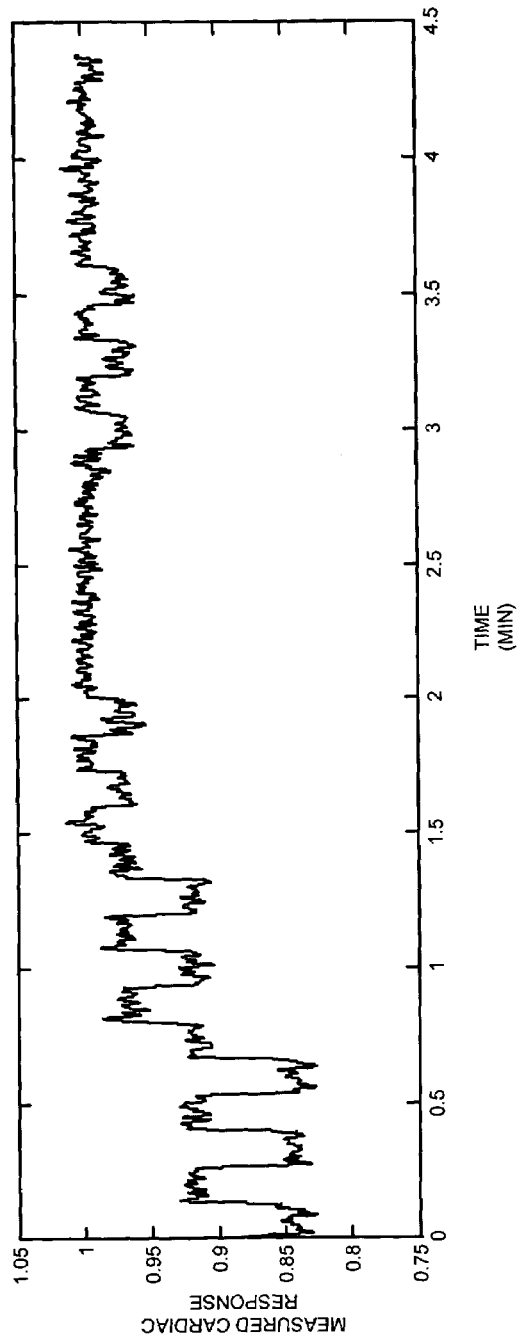
FIG. 22 is a graph showing cardiac performance using the adaptive method of FIG. 21.

By employing the gradient-based approached of FIG. 20, rapid optimization may be achieved without needing to test values throughout an entire range possible parameter values. An example of AV delay optimization is set forth in FIGS. 21-22. Test AV delay values are shown in FIG. 21. Resulting simulated cardiac response values are shown in FIG. 22. Briefly, the device paces the heart while alternating between AV delay values of 80 ms and 100 ms. As illustrated in the example of FIG. 22, 100 ms provides superior cardiac performance than 80 ms and so, during a next iteration, the device alternates between 100 ms and 120 ms. This procedure is repeated until the device settles on values of 140 ms and 160 ms, which are then averaged together to yield an optimal value of 150 ms. In this example, a fixed step size of 20 ms is used. Other step sizes are of course possible. To speed convergence, a variable step size may used, for example, by making the size of the difference between the AV delay values proportional to the difference in cardiac response obtained with the previous comparison. In this manner the device will make large steps when it is far from the optimal AV delay value, and smaller steps as it begins to approach the optimal value. As can be appreciated, a wide range of variations to the basic gradient-based approach may be employed.

Techniques for optimizing pacing parameters by exploiting an evolutionary algorithm are set forth in U.S. Pat. No. 6,522,923 to Turcott, entitled "Methods, Systems And Devices For Optimizing Cardiac Pacing Parameters Using Evolutionary Algorithms." Aspects of the evolutionary algorithm techniques may be exploited in connection with the present invention and U.S. Pat. No. 6,522,923 is incorporated by reference herein.

What has been described as far are various rapid optimization techniques performed by the implanted device under direct control by the external programmer, preferably during a follow-up session between patient and physician. Alternatively, however, any or all of the rapid optimization techniques described herein may be performed by the implanted device itself without direct control by the external programmer.

Automatic Optimization Under Control of Implanted Device

Figure 23:
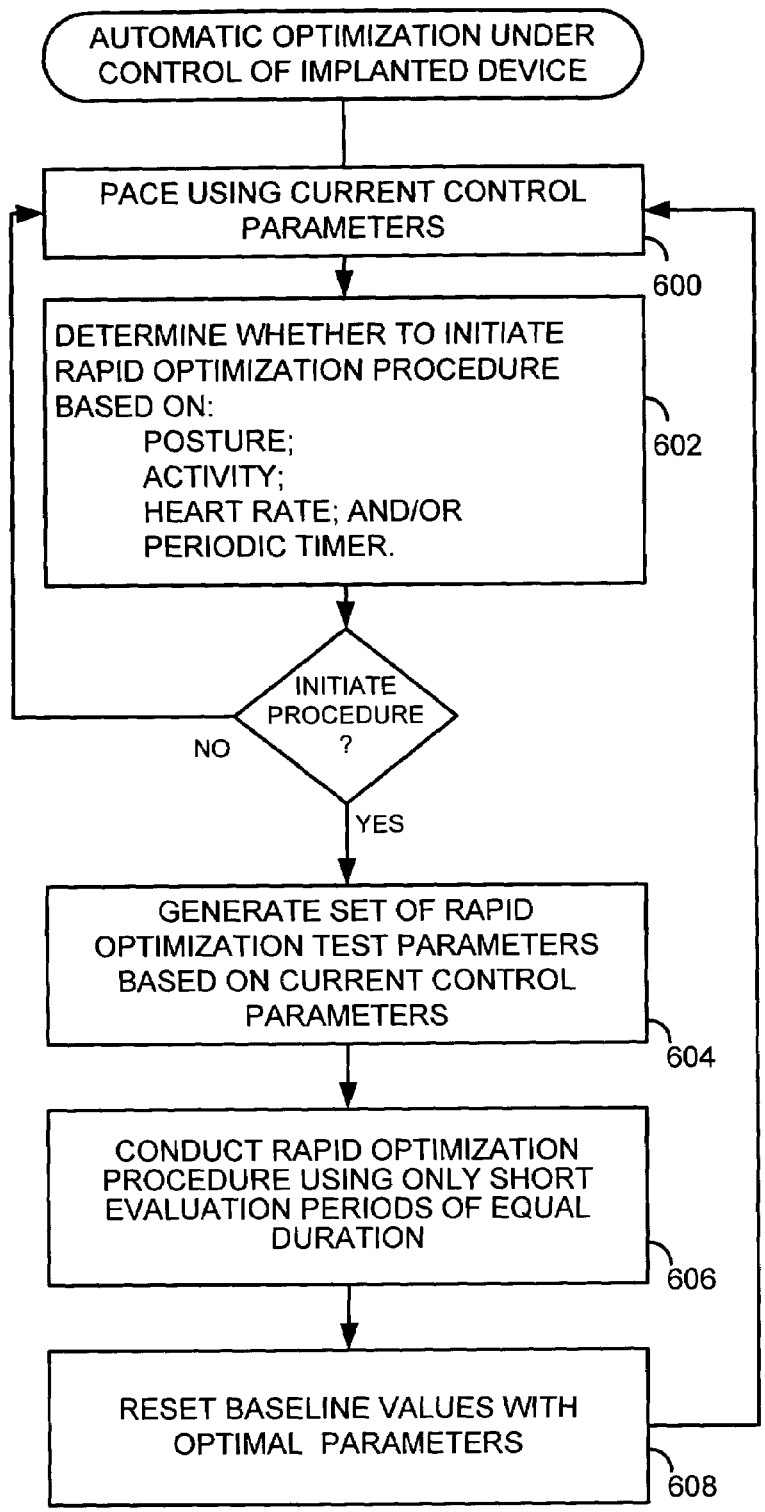
FIG. 23 is a flow chart illustrating an alternative optimization method wherein rapid optimization is automatically performed by implanted device of FIG. 5 without direct control by the external programmer of FIG. 6.

FIG. 23 illustrates a rapid optimization procedure performed automatically by an implanted device. Briefly, step 600, the implanted device paces using current reference control parameters and, at step 602, determines whether to initiate an automatic rapid parameter optimization (assuming that automatic optimization has already been enabled in the device via commands previously sent from an external programmer.) The determination of whether to trigger automatic parameter optimization is based on, for example, any significant change in posture, activity level, heart rate, fluid status or autonomic tone. Changes in posture may be detected using techniques set forth in: U.S. patent application Ser. No. 10/329,233, of Koh et al. entitled "System And Method For Determining Patient Posture Based On 3-D Trajectory Using An Implantable Medical Device", filed Dec. 23, 2002, which is incorporated herein by reference. Activity or activity variance may be detected using techniques described in U.S. Pat. No. 5,476,483, to Bornzin et al., entitled "System and Method for Modulating the Base Rate During Sleep for a Rate-responsive Cardiac Pacemaker", which is also incorporated herein by reference. Changes in autonomic tone can be assessed by heart rate variability (HRV). Changes in fluid status can be detected by pressure or photoplethysmography. Both can be indirectly detected by monitoring heart rate. Activation based on posture or heart rate is preferred since changes in autonomic tone and fluid status can happen quite slowly. Additionally or alternatively, optimization may be performed periodically, such as every five or ten minutes. Also, look-up tables can be employed to retrieve previously stored and calculated optimized values based on certain postures, heart rates, etc.

Assuming rapid optimization is to be performed then, at step 604, the on-board rapid optimizer (unit 101 of FIG. 5) implanted device generates a set of optimization test parameters based upon the current reference control parameters. In other words, at step 604, the implanted device performs the same set-up technique otherwise performed by the external programmer at step 306 of FIG. 7. In any case, at step 606, the implanted device then performs the rapid optimization procedure while monitoring cardiac performance to determine the set test parameters that optimize cardiac performance. The rapid optimization may exploit any of the techniques described elsewhere herein, such as any of the techniques of FIGS. 8-22. At step 608, the optimal parameters are then used to reset the reference values for subsequent pacing and processing return step 600.

Since optimization is performed automatically by the implanted device itself, it may be desirable to restrict the range of values through which optimization may be performed as compared to the range used in conjunction with rapid optimization preferred under the supervision of the physician. This helps prevent the device from being automatically reset to pacing control parameters that may be outside of a range that the physician would otherwise deem acceptable. Any limitations on the scope of automatic rapid optimization testing may be programmed in advance by the physician using the external programmer. Also preferably, the results of all rapid optimization procedures are stored in memory for subsequent review by the physician during a follow-up session or via transtelephonic monitoring.

In any case, automatic rapid optimization ensures that pacing control parameters are frequently adjusted so as to compensate for changes in posture or patient activity levels and to also compensate for progression or regression of heart disease in the patient as well as to compensate for any changes in cardiac performance that may be brought on by medication or disease progression.

Summary of Rapid Optimization Techniques

Figure 24:
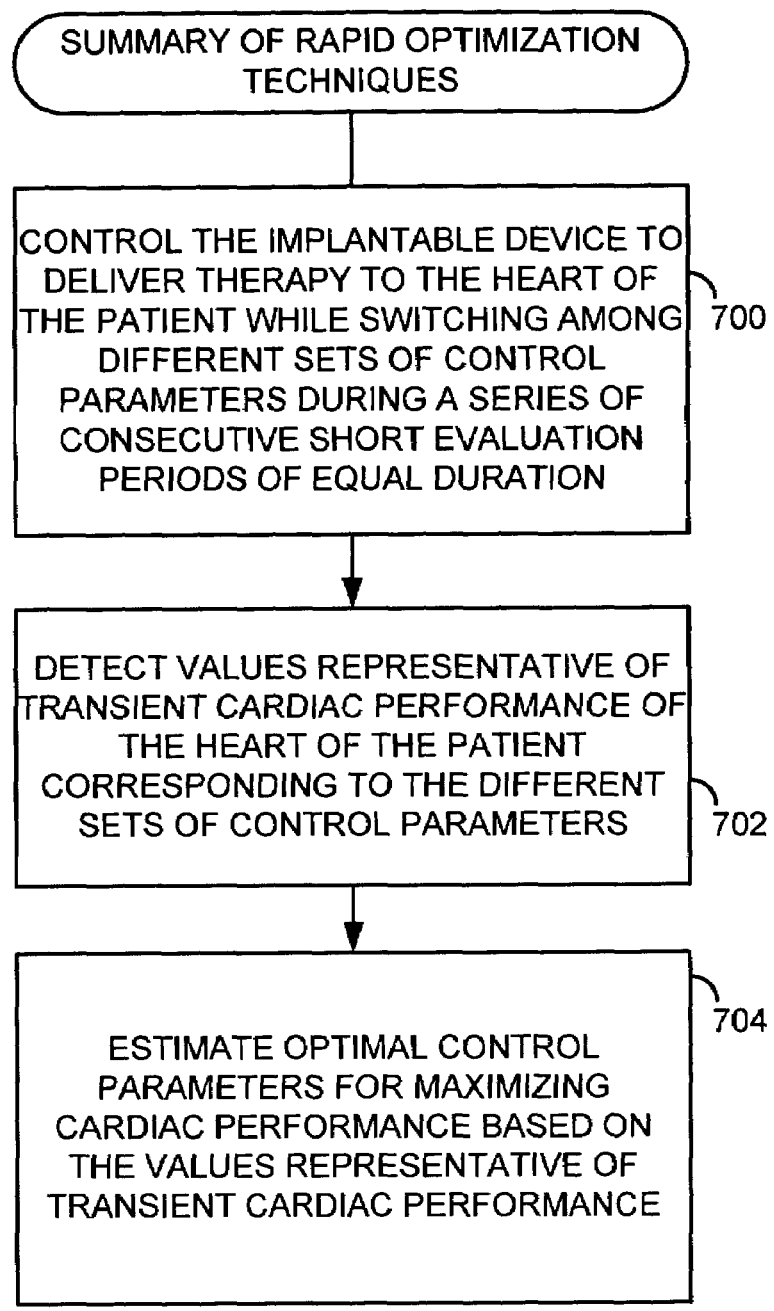
FIG. 24 is a flow chart summarizing the general technique of the invention.

FIG. 24 provides an overview of the broad techniques of the invention provided for rapidly optimizing pacing control parameters of an implantable cardiac stimulation device. Briefly, at step 700, the implantable device is controlled to deliver therapy while switching among different sets of control parameters during a series of consecutive short evaluation periods of equal duration. At step 702, values representative of transient cardiac performance of the heart of the patient are detected for the different sets of control parameters. At step 704, optimal control parameters for maximizing cardiac performance are then estimated based on the values representative of transient cardiac performance.

The various functional components of the exemplary system may be implemented using any appropriate technology including, for example, microprocessors running software programs or application specific integrated circuits (ASICs) executing hard-wired logic operations. Although described with respect to pacemakers and ICDs used in conjunction with an external programmer, aspects of the invention are applicable to other systems, such as systems employing other implantable cardiac stimulation devices or systems employing other types of external interfaces for use with the implantable device. The exemplary embodiments of the invention described herein are merely illustrative of the invention and should not be construed as limiting the scope of the invention.

What is claimed is:

1. A method for identifying preferred control parameters for use in controlling an implantable cardiac stimulation device for implant within a patient, the method comprising the steps of:

controlling the implantable device to deliver therapy to the heart of the patient during a series of consecutive periods that are substantially equal in duration to one another and less than about 12 seconds each in duration by alternating, from one evaluation period to another, between different sets of selected test control parameters and a set of reference control parameters;

detecting values representative of transient cardiac performance corresponding to the different sets of control parameters during the evaluation periods; and estimating optimal control parameters for maximizing cardiac performance based on a difference between the values representative of transient cardiac performance during each consecutive pair of evaluation periods.

2. The method of claim 1 wherein the evaluation periods are sufficiently short so that hemodynamic feedback systems of the patient do not have time to readjust the cardiovascular system of the patient to a substantially equilibrium state before the control parameters are switched again.

3. The method of claim 1 wherein the evaluation periods are no longer than two respiratory cycles each, wherein a respiratory cycle comprises one inspiration and one expiration.

4. The method of claim 2 wherein the step of detecting values representative of transient cardiac performance is performed to detect changes in transient cardiac performance from one consecutive evaluation period to another; and wherein the step of estimating the optimal set of control parameters is performed based on the changes in transient cardiac performance.

5. The method of claim 4 wherein the step of detecting changes in transient cardiac performance comprises the steps of:

measuring values representative of transient cardiac performance of the heart of the patient during each evaluation period; and determining the difference in transient cardiac performance based on a comparison of the measured values.

6. The method of claim 5 wherein the periods of time over which the values representative of transient cardiac performance are measured are each set equal to substantially identical portions of a respiratory cycle, wherein a respiratory cycle comprises one inspiration and one expiration.

7. The method of claim 5 wherein the periods of time over which the values representative of transient cardiac performance are measured are each set equal to about four seconds.

8. The method of claim 5 wherein the step of determining the difference in transient cardiac performance based on a comparison of the measured values includes the steps performed, for each evaluation period employing test control parameters, of:
generating a first difference value representative of a change in average transient cardiac performance between the prior reference evaluation period and the given evaluation period;
generating a second difference value representative of a change in average transient cardiac performance between the given evaluation period and the subsequent reference evaluation period and reversing the sign of the second difference value such that a pair of first and second difference values are generated for each evaluation period.

9. The method of claim 8 wherein the step of estimating the optimal set of control parameters includes the steps of:
associating each pair of first and second difference values with the set of control parameters employed during the corresponding evaluation period;
fitting a curve to the difference values versus associated test parameter values; and
identifying the set of control parameters providing a maximal difference value as indicated by the curve.

10. The method of claim 5 wherein the step of controlling the implantable device to deliver therapy using different sets of control parameters is performed by cycling through different sets of selected test control parameters to provide for all possible changes between sets of control parameters.

11. The method of claim 5 wherein the step of controlling the implantable device to deliver therapy using different sets of control parameters is performed by cycling through different sets of selected test control parameters to provide for only a sub-set of all possible changes between sets of control parameters.

12. The method of claim 5 wherein the step of determining the difference in transient cardiac performance based on a comparison of the measured values includes the steps of:
detecting a value representative of transient cardiac performance during an immediately preceding evaluation period;
detecting a value representative of transient cardiac performance during the given evaluation period; and
generating a difference value representative of a change in transient cardiac performance between the prior evaluation period and the given evaluation period such that a single difference value is generated for each evaluation period.

13. The method of claim 12 wherein the step of estimating the optimal set of control parameters includes the steps of:
associating each difference value with the set of control parameters employed during the corresponding evaluation period;
fitting a single curve to the difference values versus associated test parameter values; and
identifying a set of preferred control parameters providing maximal difference values as indicated by the single curve.

14. The method of claim 12 wherein the step of estimating the optimal set of control parameters includes the steps of:
associating each difference value with the set of control parameters employed during the corresponding evaluation period;
for each set of control parameters, fitting a separate curve to the difference values versus the set of parameter values; and
for each set of control parameters, identifying a separate set of preferred control parameters providing maximal difference values as indicated by the separate curve; and
averaging the separate sets of preferred control parameters together to yield a single set of control parameters.

15. The method of claim 1
wherein the step of controlling the implantable device to deliver therapy while switching control parameters is performed to adaptively adjust the control parameters based on resulting changes in cardiac performance; and
wherein the step of estimating optimal control parameters for maximizing cardiac performance comprises identifying control parameters that result in the most positive difference in cardiac performance as compared to all other control parameter values.

16. The method of claim 1 wherein the control parameters include one or more of: pacing base rate; maximum tracking rate; minimum tracking rate; atrioventricular (AV) delay and interventricular delay.

17. The method of claim 1 wherein the step of detecting values representative of transient cardiac performance is performed to detect values representative of one or more of stroke volume, cardiac output, end-diastolic volume, end-systolic volume, ejection fraction, cardiac output index, flow through the mitral valve, maximum rate of change of left ventricular pressure with time, maximum rate of change of aortic pressure with time, mean arterial pressure, arterial pulse pressure, vascular volume, and vascular photoplethysmography.

18. The method of claim 1 further including the initial step of determining whether to initiate an optimization procedure based on a change in one or more of patient posture, heart rate, activity levels, autonomic tone, and fluid status.

19. The method of claim 1 wherein the steps of the method are performed periodically.

20. The method of claim 1 wherein the step of controlling the implantable device to deliver therapy to the heart of the patient while changing control parameters is performed by an external programmer device.

21. The method of claim 1 wherein all steps of the method are performed by the implantable device.

* * * * *